(12) United States Patent
Akagawa et al.

(10) Patent No.: US 10,429,244 B2
(45) Date of Patent: Oct. 1, 2019

(54) LIGHT MEASUREMENT DEVICE

(71) Applicant: NEC Corporation, Tokyo (JP)

(72) Inventors: Takeshi Akagawa, Tokyo (JP); Masahiro Kubo, Tokyo (JP); Katsumi Abe, Tokyo (JP); Kimiyasu Takoh, Tokyo (JP); Ersin Altintas, Tokyo (JP); Yuji Ohno, Tokyo (JP); Tetsuri Ariyama, Tokyo (JP)

(73) Assignee: NEC Corporation, Tokyo (JP)

( * ) Notice: Subject to any disclaimer, the term of this patent is extended or adjusted under 35 U.S.C. 154(b) by 47 days.

(21) Appl. No.: 15/559,872

(22) PCT Filed: Mar. 17, 2016

(86) PCT No.: PCT/JP2016/001540
§ 371 (c)(1),
(2) Date: Sep. 20, 2017

(87) PCT Pub. No.: WO2016/152108
PCT Pub. Date: Sep. 29, 2016

(65) Prior Publication Data
US 2018/0058938 A1    Mar. 1, 2018

(30) Foreign Application Priority Data
Mar. 25, 2015    (JP) ................ 2015-062054

(51) Int. Cl.
*G01J 9/02* (2006.01)
*G01B 9/02* (2006.01)
(Continued)

(52) U.S. Cl.
CPC ............ *G01J 9/02* (2013.01); *G01B 9/02091* (2013.01); *G01N 21/4133* (2013.01); *G01N 21/45* (2013.01); *G01N 2021/4186* (2013.01)

(58) Field of Classification Search
CPC ... G01J 9/02; G01B 9/02091; G01N 21/4133; G01N 21/45
See application file for complete search history.

(56) References Cited

U.S. PATENT DOCUMENTS 6,891,149 B1 * 5/2005 Lewis ............... G01J 9/02
                                           250/216
2005/0243327 A1 * 11/2005 Li ................. A61B 5/0059
                                           356/496
(Continued)

FOREIGN PATENT DOCUMENTS

JP    H05-149719 A    6/1993
JP    H0815130 A      1/1996
(Continued)

OTHER PUBLICATIONS

English Machine Translation of JP 2010007812 (Year: 2010).*
(Continued)

*Primary Examiner* — Dominic J Bologna
(74) *Attorney, Agent, or Firm* — Wilmer Cutler Pickering Hale and Dorr LLP

(57) ABSTRACT

[Object]
To obtain interference light having a stronger light intensity, and to more accurately measure a refractive index of a measured object, with a simplified configuration.
[Solution Means]
A light measurement device 100 includes a phase adjustment unit 120 and a detector 140. The phase adjustment unit 120 outputs reference light E(R) based on object light E1 being light to be obtained by transmission or reflection of light E from a light source with respect to a measured object 200, and signal light E(S) whose phase is adjusted to be different from a phase of signal light. The detector 140 derives a transmission or reflection light intensity distribution or a refractive index of the measured object 200, based on
(Continued)

interference light E2 between signal light E(S) and reference light E(R) to be output by the phase adjustment unit 120. An optical axis of light E from a light source is linearly disposed. The phase adjustment unit 120 and the detector 140 are disposed on the optical axis of light E from a light source.

13 Claims, 8 Drawing Sheets

(51) Int. Cl.
*G01N 21/41* (2006.01)
*G01N 21/45* (2006.01)

(56) References Cited

U.S. PATENT DOCUMENTS

| | | | | |
|---|---|---|---|---|
| 2007/0159637 | A1* | 7/2007 | Toida | A61B 5/0066 |
| | | | | 356/456 |
| 2008/0212103 | A1* | 9/2008 | Walmsley | G01J 11/00 |
| | | | | 356/450 |
| 2008/0309946 | A1* | 12/2008 | Chou | G01B 9/02002 |
| | | | | 356/487 |
| 2012/0105852 | A1* | 5/2012 | Patil | G01N 21/253 |
| | | | | 356/445 |
| 2012/0200901 | A1 | 8/2012 | Dubois et al. | |

FOREIGN PATENT DOCUMENTS

| | | |
|---|---|---|
| JP | 2005-148027 A | 6/2005 |
| JP | 2006-084233 A | 3/2006 |
| JP | 2008-541124 A | 11/2008 |
| JP | 2009-139352 A | 6/2009 |
| JP | 2010-007812 A | 1/2010 |
| JP | 2012-078100 A | 4/2012 |
| JP | 2012-083394 A | 4/2012 |
| JP | 2013-507647 A | 3/2013 |
| JP | 2013-541021 A | 11/2013 |
| JP | 2014-048096 A | 3/2014 |
| WO | WO-2006/123148 A1 | 11/2006 |
| WO | WO-2011/042442 A1 | 4/2011 |
| WO | WO-2012/057681 A1 | 5/2012 |

OTHER PUBLICATIONS

English Machine Translation of JP 2006084233 (Year: 2003).*
English Machine Translation of JP 2005148027 (Year: 2005).*
International Search Report, Corresponding to PCT/JP2016/001540, dated May 31, 2016, 2 pp.

* cited by examiner

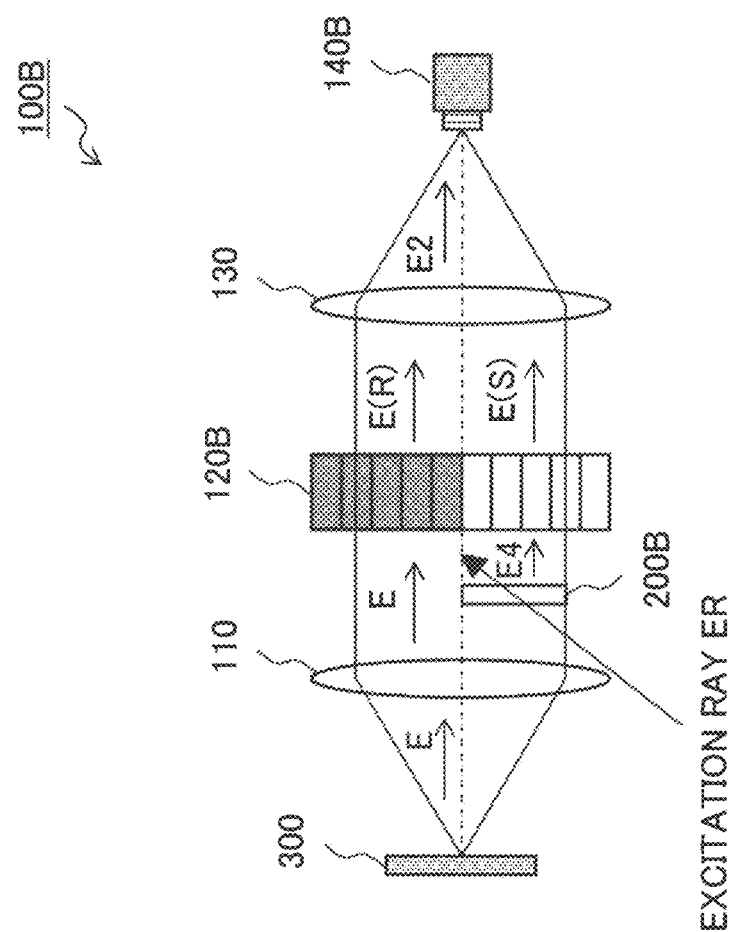

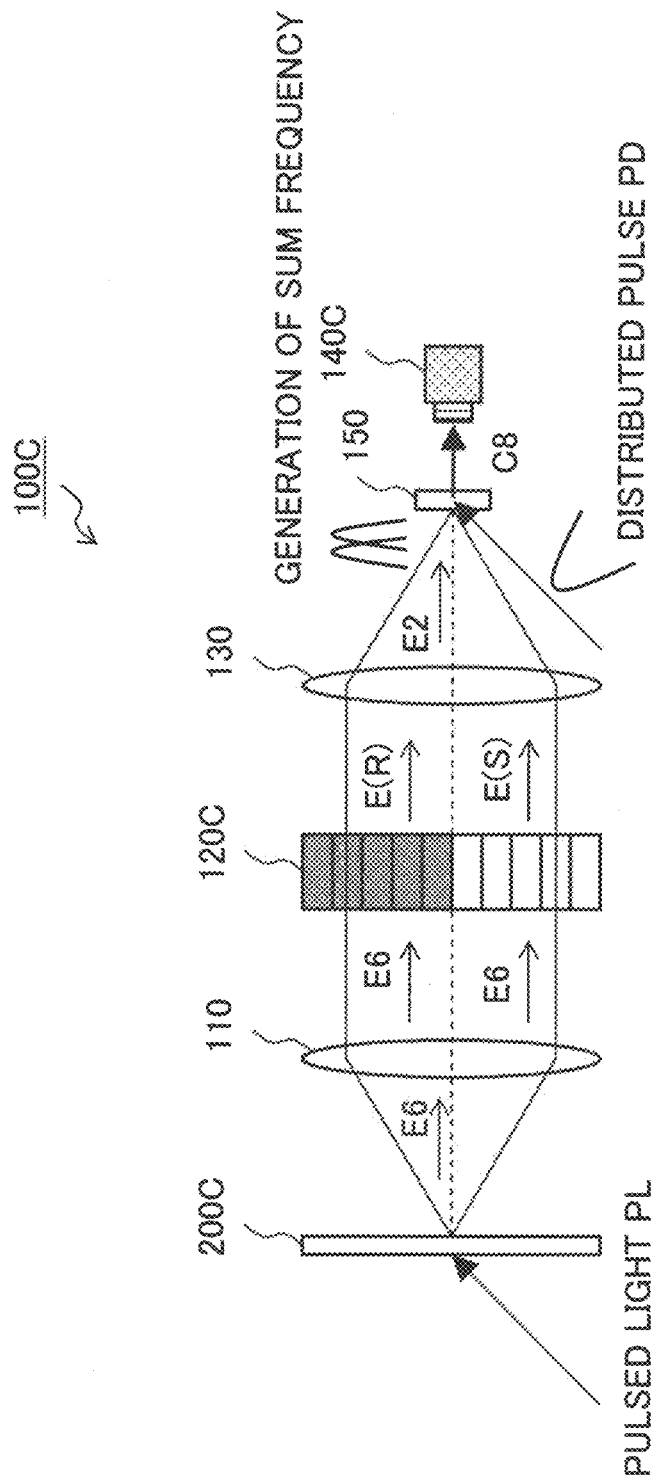

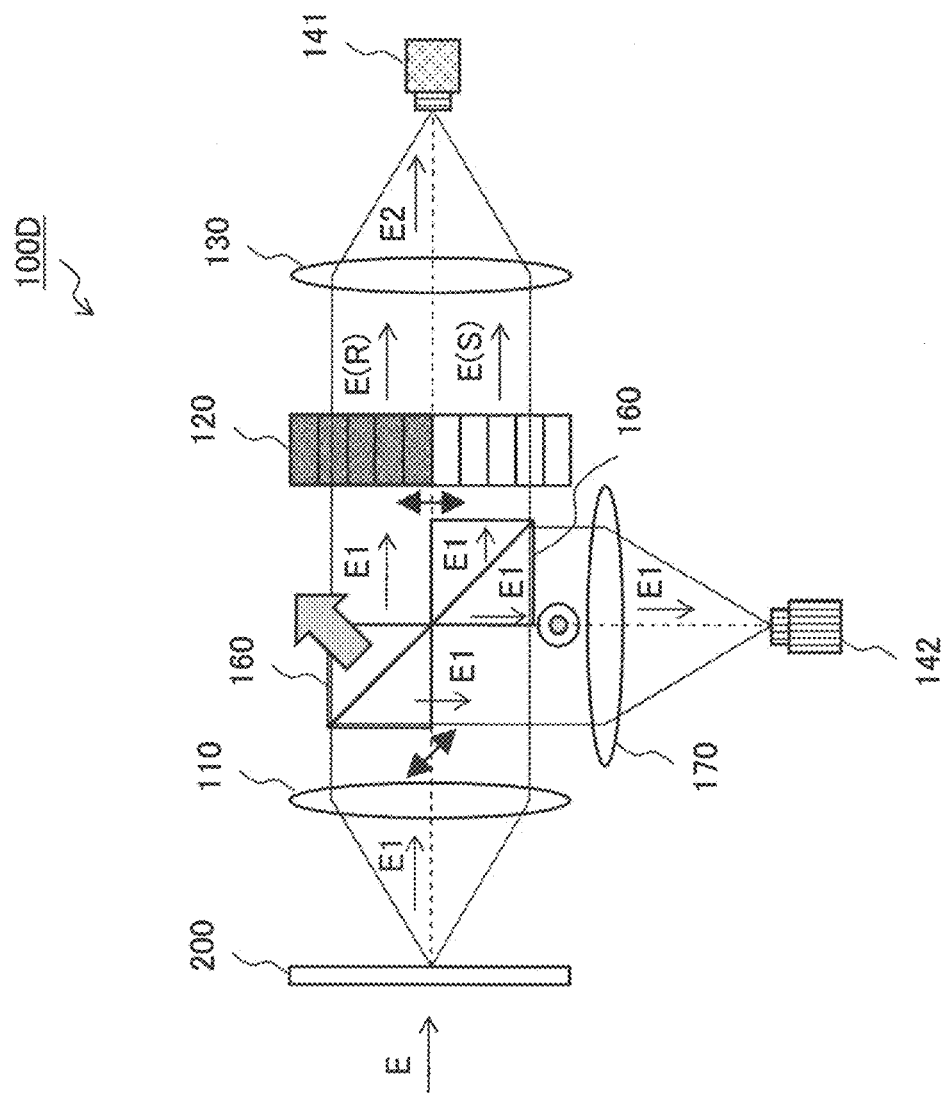

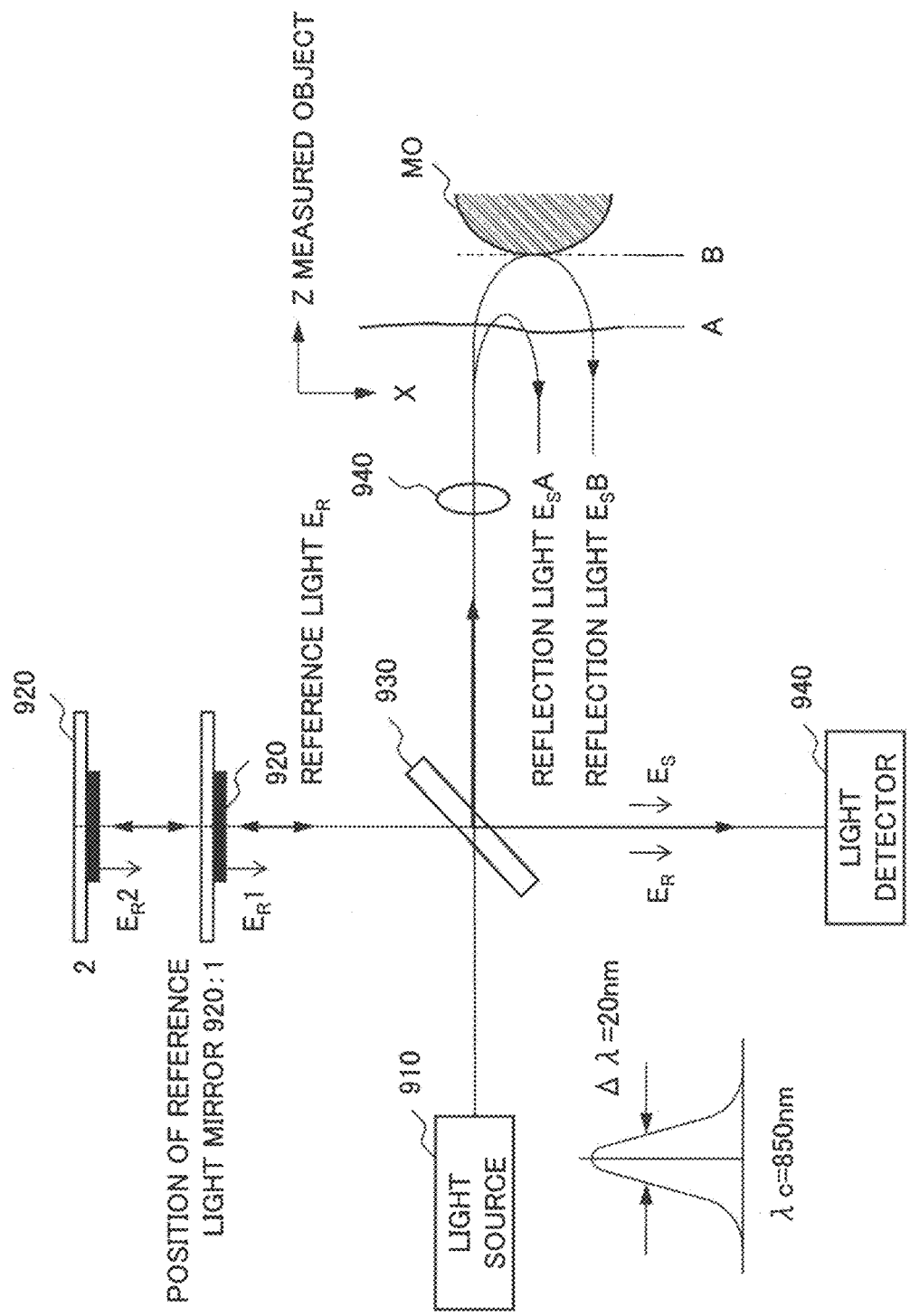

LIGHT MEASUREMENT DEVICE

CROSS-REFERENCE TO RELATED APPLICATIONS

The present application is a national stage application of International Application No. PCT/JP2016/001540 entitled "Light Measurement Device," filed on Mar. 17, 2016, which claims the benefit of priority from Japanese Patent Application No. JP2015-062054, filed on Mar. 25, 2015, the disclosures of which are incorporated herein in their entirety by reference thereto.

TECHNICAL FIELD

The present invention relates to a light measurement device, for instance, to a light measurement device and the like, which is configured to derive a transmission or reflection light intensity distribution or a refractive index of a measured object from interference light between signal light to be obtained by transmission or reflection of light from a light source with respect to the measured object, and reference light.

BACKGROUND ART

In recent years, a technique on an optical coherence tomography (OCT) is widely used in a field of funduscopic examination or the like. The OCT is a technique capable of non-invasively imaging a tomographic image of a living body skin of 1 to 2 mm-depth with a spatial resolution of about 10 μm. The OCT is based on an interferometer using low coherent light. Further, the OCT selectively detects a straight advancing light component obtained by radiation of light on a living tissue and reflection of the light from an inside of the tissue, and forms a two-dimensional or three-dimensional tomographic image, based on the detection.

FIG. 8 is a conceptual diagram illustrating a basic configuration of the OCT (e.g. see NPL 1). As illustrated in FIG. 8, the basic configuration of the OCT includes a light source 910, a reference light mirror 920, a beam splitter 930, and a light detector 940. A measured object MO is a living body, for example.

The light source 910 emits low coherent light in a near-infrared range. Low coherent light is light whose timewise coherence is extremely low. Note that the light source 910 includes a super luminescent diode (SLD), for example.

As illustrated in FIG. 8, the light source 910 emits low coherent light toward the beam splitter 930. Low coherent light in this case has a central wavelength $\lambda_C$=850 nm, and a spectral full width at half maximum $\Delta\lambda$=20 nm, for example.

Light source light is split into two beams by the beam splitter 930. One beam of the split light source light is directed toward the reference mirror 920, is reflected on the reference mirror 920, and then returns to the beam splitter 930 as reference light $E_R$. The other beam of the split light source light is radiated on the measured object MO as measurement light. A multitude of beams of reflection light (signal light) $E_S$ (reflection light $E_SA$ and $E_SB$, as an example) from a surface and an inside of the measured object MO return to the beam splitter 930. A half of reference light $E_R$ and a half of reflection light $E_S$ that return to the beam splitter 930 have optical paths coincident with each other, and interfere with each other on the front side of the light detector 940.

Herein, as illustrated in FIG. 8, specific reflection surfaces on the surface and the inside of the measured object MO along a propagation direction of signal light are defined as A and B.

When it is assumed that the reflection surface A inside the measured object MO, and a position 1 of the reference light mirror 920 are optically equidistant with respect to the beam splitter 930, time zones of sinusoidal vibration of reference light $E_R 1$ and reflection light $E_S A$ are superimposed each other, and the reference light $E_R 1$ and the reflection light $E_S A$ interfere with each other. Consequently, the detector 940 obtains interference light between the reference light $E_R 1$ and the reflection light $E_S A$. Next, in order to obtain interference light from reflection light $E_S B$, the reference light mirror 920 is moved in a direction to be away from the beam splitter 930 up to a position 2 where a reflection point B and the reference light mirror 920 are equidistant. In this way, sequentially moving the reference light mirror 920 to allow the detector 940 to detect interference light makes it possible to obtain a reflection light intensity distribution in an optical axis direction. As described above, the OCT is generally used for tomographic imaging. Although light interference is used, the OCT is not positively used for deriving a refractive index of a measured object.

Note that PTLs 1 to 4 also disclose a technique associated with the present invention.

CITATION LIST

Non Patent Literature

[NPL 1] Edited by the IEEJ Investigation Committee on Next Generation Biomedical Laser Applications, "Biomedical Photonics", first edition by the Institute of Electrical Engineers of Japan, Apr. 30, 2009, P.P. 126-129

Patent Literature

[PTL 1] Japanese Laid-open Patent Publication No. 2014-048096
[PTL 2] Japanese Laid-open Patent Publication No. 2012-078100
[PTL 3] Japanese Laid-open Patent Publication No. 2009-139352
[PTL 4] Japanese Laid-open Patent Publication No. H08-015130

SUMMARY OF INVENTION

Technical Problem

However, in the OCT illustrated in FIG. 8, there is a problem that the structure becomes complicated because a mechanical adjustment operation such as moving the reference light mirror 920 to adjust an optical path length is needed, and the reference light mirror 920 and the beam splitter 930 are necessary. Further, as described above, a half of reference light $E_R$ and a half of reflection light $E_S$ that return to the beam splitter 930 interfere with each other on the front side of the light detector 940 before incidence on the light detector 940. However, the remaining half of the reference light $E_R$ and the remaining half of the reflection light $E_S$ propagate in a direction different from the direction to the light detector 940, and are not used for interference. Therefore, use efficiency of a light amount is not high.

The present invention has been made in view of the aforementioned circumstance, and an object of the present invention is to provide a light measurement device that enables to derive a reflection light intensity distribution or a refractive index of a measured object with a simplified configuration.

Solution to Problem

A light measurement device according to the present invention includes a phase adjustment unit configured to adjust a phase difference between signal light and reference light, the signal light being based on object light being light to be obtained by transmission or reflection of light from a light source with respect to a measured object, the reference light being for use in obtaining interference light with respect to the signal light; and a detector configured to detect interference light between the signal light and the reference light to be output by the phase adjustment unit, and derive a transmission or reflection light intensity distribution or a refractive index of the measured object, based on the detected interference light. An optical axis of light from the light source or the object light is linearly disposed. The phase adjustment unit and the detector are disposed on an optical axis of the light from the light source or the object light.

Advantageous Effects of Invention

According to the technique of the present invention, it is possible to derive a transmission or reflection light intensity distribution or a refractive index of a measured object with a simplified configuration.

BRIEF DESCRIPTION OF DRAWINGS

FIG. 5 is a diagram schematically illustrating a configuration of a light measurement device in a second exemplary embodiment of the present invention;

FIG. 6 is a diagram schematically illustrating a configuration of a light measurement device in a third exemplary embodiment of the present invention;

FIG. 7 is a diagram schematically illustrating a configuration of a light measurement device in a fourth exemplary embodiment of the present invention; and FIG. 8 is a conceptual diagram illustrating a basic configuration of an OCT.

DESCRIPTION OF EMBODIMENTS

Exemplary Embodiment Illustrating Concept

Figure 1:
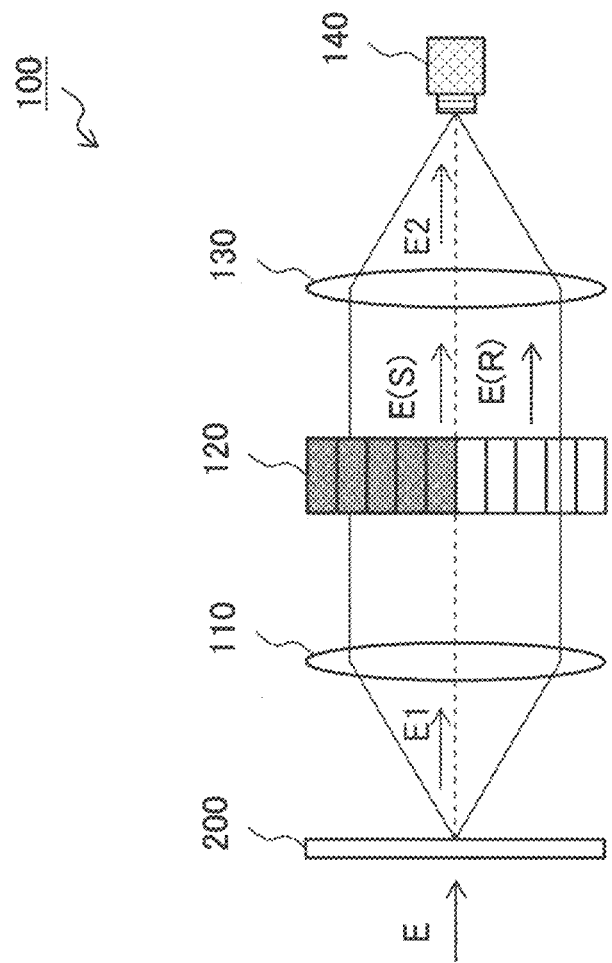
FIG. 1 is a diagram schematically illustrating a configuration of a light measurement device in an exemplary embodiment illustrating a concept of the present invention.

FIG. 1 is a diagram schematically illustrating a configuration of a light measurement device 100 in an exemplary embodiment illustrating a concept of the present invention.

As illustrated in FIG. 1, the light measurement device 100 includes a first lens 110, a phase adjustment unit 120, a second lens 130, and a detector 140. Note that as will be described later, the first lens 110 and the second lens 130 may be omitted. Specifically, in a case where the beam diameter of object light from a measured object 200 is sufficiently large to such an extent that the phase adjustment unit can function properly, as compared with a sectional area of the phase adjustment unit 120 in an optical axis direction, the first lens 110 and the second lens 130 are not essential constituent elements.

As illustrated in FIG. 1, the measured object 200 is disposed on the front side of the first lens 110, as a measurement object for the light measurement device 100. Examples of the measured object 200 are a liquid, a living body and the like. The measured object 200, however, is not limited to the above, as far as the measured object transmits or reflects light. When light E from a light source transmits through or is reflected from the measured object 200, object light E1 is generated. Specifically, object light E1 is light to be obtained when light E from the light source transmits through or is reflected from the measured object 200.

As illustrated in FIG. 1, the first lens 110, the phase adjustment unit 120, the second lens 130, and the detector 140 are linearly disposed on the optical axis of object light E1. For instance, in a case of transmission where the measured object 200 is disposed perpendicularly to light E from a light source, refraction does not occur within the measured object 200. Therefore, the optical axis of light E from a light source, and the optical axis of object light E1 may coincide with each other.

Note that the optical axes of the first lens 110 and the second lens 130 are disposed to overlap the optical axis of object light E1 from a light source. In case of reflection, it is possible to linearly dispose, on the optical axis of object light E1, the phase adjustment unit 120, the second lens 130, and the detector 140 which follow the first lens 110 by radiating light E from a light source on the measured object 200 and allowing object light E1, which is reflection light from the measured object 200, to be incident normal to the first lens 110. Further, as light E from a light source, for instance, near infrared light in the range of from about 0.78 µm to 2.5 µm is used. Note that as light E from a light source, it is also possible to use ultraviolet light (in the range of from about 0.01 µm to 0.38 µm), visible light (in the range of from about 0.38 µm to 0.78 µm), mid infrared light (in the range of from about 2.5 µm to 25 µm), or far infrared light (in the range of from about 25 µm to 100 µm) other than the above.

As illustrated in FIG. 1, the first lens 110 is disposed between the measured object 200 and the phase adjustment unit 120. Further, the first lens 110 is disposed along the optical axis of object light E1. Object light E1 being light to be obtained by transmission or reflection of light E from a light source with respect to the measured object 200 is incident on the first lens 110. The first lens 110 converts incident object light E1 into a parallel light flux. The first lens 110 is made of glass or a resin material.

As illustrated in FIG. 1, the phase adjustment unit 120 is disposed between the first lens 110 and the second lens 130. Further, the phase adjustment unit 120 is disposed on the optical axis of object light E1. Object light E1 as a parallel light flux obtained by conversion by the first lens 110 is incident on the phase adjustment unit 120. The phase adjustment unit 120 adjusts the phase of a part of object light E1 to be incident by the first lens 110. The phase adjustment unit 120 adjusts the phase difference between signal light E(S) and reference light E(R), wherein the signal light E(S)

is based on object light E1 being light to be obtained by transmission or reflection of light E from a light source with respect to the measured object 200, and the reference light E(R) is used for obtaining interference light E2 (to be described later) with the signal light E(S).

Herein, the phase adjustment unit 120 generates a phase difference between an upper portion of object light E1 and a lower portion of the object light E1 by applying different modulations to the upper portion (on the upper side on the plane of FIG. 1) of the object light E1 above the center of the phase adjustment unit 120, and to the lower portion (on the lower side on the plane of FIG. 1) of the object light E1 below the center of the phase adjustment unit 120. For instance, the phase adjustment unit 120 may generate a phase difference by modulating both of an upper portion (on the upper side on the plane of FIG. 1) of object light E1 above the center of the phase adjustment unit 120, and a lower portion (on the lower side on the plane of FIG. 1) of object light E1 below the center of the phase adjustment unit 120. Alternatively, the phase adjustment unit 120 may adjust the phase of an upper portion (on the upper side on the plane of FIG. 1) of object light E1 above the center of the phase adjustment unit 120 by modulating only the upper portion (on the upper side on the plane of FIG. 1) of the object light E1 above the center of the phase adjustment unit 120, and may not adjust the phase of a lower portion (on the lower side on the plane of FIG. 1) of the object light E1 below the center of the phase adjustment unit 120.

Note that the exemplary embodiment is not limited to the above. The phase adjustment unit 120 may adjust the phase of a lower portion (on the lower side on the plane of FIG. 1) of object light E1 below the center of the optical path of the object light E1, and may not adjust the phase of an upper portion (on the upper side on the plane of FIG. 1) of the object light E1 above the center of the optical path of the object light E1. Alternatively, the phase adjustment unit 120 may adjust the phase of object light E1 in a center portion of an optical path, and may not adjust the phase of the object light E1 in an outer peripheral portion of the optical path. Conversely, the phase adjustment unit 120 may not adjust the phase of object light E1 in a center portion of an optical path, and may adjust the phase of the object light E1 in an outer peripheral portion of the optical path.

In a case where the phase adjustment unit 120 modulates only an upper portion (on the upper side on the plane of FIG. 1) of object light E1 or a lower portion (on the lower side on the plane of FIG. 1) of the object light E1 with respect to the center of the phase adjustment unit 120, for instance, the phase adjustment unit 120 outputs object light E1 after phase adjustment by the phase adjustment unit 120 as reference light E(R), and outputs object light E1 whose phase is not adjusted by the phase adjustment unit 120 as signal light E(S).

In this case, the phase adjustment unit 120 adjusts and outputs light in such a manner that the light amount of reference light E(R) after phase adjustment of object light E1 is equal to the light amount of signal light E(S) whose phase is not adjusted.

The phase adjustment unit 120 includes a spatial light modulator, for instance. The spatial light modulator (SLM) can two-dimensionally control the phase of light. The spatial light modulator internally includes a liquid crystal unit. The spatial light modulator changes the optical path length of a part of incident light by controlling the refractive index of the liquid crystal unit provided therein. Consequently, the phase of light incident on the spatial light modulator is adjusted. In this case, the spatial light modulator finely adjusts a channel to be controlled or a channel not to be controlled the spatial light modulator in such a manner that the light amount of reference light E(R) after phase adjustment by the phase adjustment unit 120 is equal to the light amount of signal light E(S) whose phase is not adjusted. Further, positions of the measured object 200, the first lens 110, the second lens 130, and the detector 140 are also adjusted. Herein, a spatial light modulation unit imposes a phase shift by a channel to be controlled.

In a case where a spatial light modulator is of a transmission type, the spatial light modulator has features such that the spatial light modulator can dominantly modulate the phase of light, control each space, obtain a high light use efficiency, miniaturize the device, and is controllable by a simplified computer. Note that a spatial light modulator may not be of a transmission type but may be of a reflection type.

Further, a micro-optical element may be used in place of a liquid crystal unit (not illustrated) of a spatial light modulator. Examples of the micro-optical element are micro electro mechanical systems (MEMS), a silicon device, and a compound device.

As illustrated in FIG. 1, the second lens 130 is disposed between the phase adjustment unit 120 and the detector 140. The second lens 130 is disposed on an optical path of reference light E(R) and signal light E(S). The second lens 130 collects reference light E(R) and signal light E(S) to be output from the phase adjustment unit 120. Specifically, the second lens 130 collects reference light E(R) after phase adjustment by the phase adjustment unit 120, and signal light E(S) whose phase is not adjusted.

According to the aforementioned configuration, it is possible to detect, by the detector 140, light (interference light E2) generated by interference between reference light E(R) and signal light E(S) to be output by the phase adjustment unit 120. Specifically, interference light E2 is generated by interference between reference light E(R) after phase adjustment by the phase adjustment unit 120, and signal light E(S) whose phase is not adjusted. The interference light E2 is incident on the detector 140. The third lens 130 is formed of glass or a resin material.

As illustrated in FIG. 1, the detector 140 is disposed to face the second lens 130. The detector 140 is disposed on the optical axis of object light E1. Interference light E2 collected by the second lens 130 is incident on the detector 140. More specifically, interference light E2 between reference light E(R) after phase adjustment by the phase adjustment unit 120, and signal light E(S) whose phase is not adjusted is incident on the detector 140. The detector 140 detects interference light E2 between reference light E(R) and signal light E(S), and derives a refractive index or a reflection light intensity distribution of the measured object 200 based on the detected interference light E2.

More specifically, the detector 140 derives a refractive index of the measured object 200 from a change in light intensity of interference light E2. The detector 140 includes a light receiving element, for instance. Note that it may be possible to calculate light absorbance of the measured object 200 from interference light obtained by the detector 140 by operating a phase change amount to be adjusted by the phase adjustment unit 120.

Note that generally, a light intensity is distributed in a state that the center of a light beam axis has a peak intensity. In view of the above, normally, the detector 140 derives a refractive index of the measured object 200 from a change in light intensity associated with an optical axis. The exemplary embodiment, however, is not limited to the above. The detector 140 may derive a refractive index of the measured object 200 from a change in light intensity associated with a distribution other than an optical axis (e.g. a tail portion).

Figure 2:
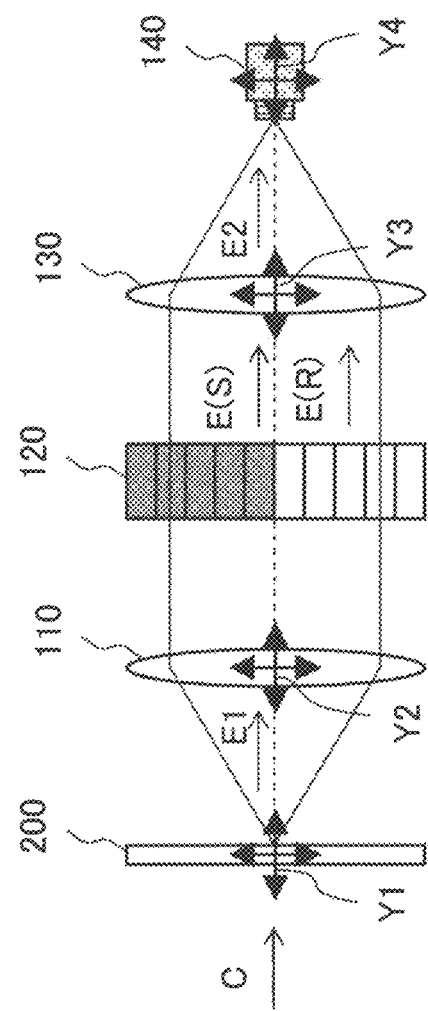
FIG. 2 is a diagram for describing an operation of the light measurement device in the exemplary embodiment illustrating the concept of the present invention.

Next, an operation of the light measurement device 100 is described. FIG. 2 is a diagram for describing an operation of the light measurement device 100.

As illustrated by arrows Y1 to Y4 in FIG. 2, positions of the first lens 110, the phase adjustment unit 120, the second lens 130, and the detector 140 are adjusted. Further, the amount of light for splitting is adjusted by adjusting a channel to be controlled by the phase adjustment unit 120. In this way, controlling optical axis adjustment and the amount of light for splitting independently of each other makes it easy to perform position adjustment and attain light amount uniformity of two beams (reference light E(R) after phase adjustment by the phase adjustment unit 130, and signal light E(S) whose phase is not adjusted).

Generally, as compared with a Michelson interferometer or a Mach-Zehnder interferometer, in an interference structure of an associate common optical path interferometer, in which improvement is necessary for optical axis adjustment or light amount uniformity corresponding to each arm, position adjustment and light amount uniformity are important elements. Satisfying requirements on these elements makes it possible to achieve improvement so as to facilitate adjustment on brightness of interference fringes of interference light E2 to be detected by the detector 140.

First of all, light E from a light source (not illustrated) is radiated on the measured object 200. Light from a light source incident on the measured object 200 transmits or reflects with respect to the measured object 200.

Further, object light E1 to be obtained by transmission or reflection of light E from a light source with respect to the measured object 200 is incident on the first lens 110.

The first lens 110 converts incident object light E1 into a parallel light flux. Object light E1 as a parallel light flux obtained by conversion by the first lens 110 is incident on the phase adjustment unit 120.

The phase adjustment unit 120 adjusts the phase of an upper portion (on the upper side on the plane of FIG. 2) of object light E1 above the center of the phase adjustment unit 120, for instance. On the other hand, the phase adjustment unit 120 does not adjust the phase of a lower portion (on the lower side on the plane of FIG. 2) of the object light E1 below the center of the phase adjustment unit 120. The phase adjustment unit 120 outputs reference light E(R) after phase adjustment by the phase adjustment unit 120, and signal light E(S) whose phase is not adjusted toward the second lens 130.

Note that, for instance, in a case where a sectional area of the phase adjustment unit 120 in an optical axis direction is as small as the beam diameter of object light E1 from the measured object 200, it is possible to omit the first lens 110. Specifically, in a case where object light E1 to be incident on the phase adjustment unit 120 is regarded as a parallel light flux, it is possible to allow incidence of the object light E1 into the phase adjustment unit 120 without converting the object light E1 into a parallel light flux. In a case where the measured object 200 is disposed far from the phase adjustment unit 120, it is also possible to omit the first lens 110 for the same reason as described above.

Next, the second lens 130 collects reference light E(R) and signal light E(S) to be output from the phase adjustment unit 120. Specifically, the second lens 130 collects reference light E(R) after phase adjustment by the phase adjustment unit 120, and signal light E(S) whose phase is not adjusted. Then, reference light E(R) and signal light E(S) to be output by the phase adjustment unit 120 interfere with each other.

Specifically, reference light E(R) and signal light E(S) interfere with each other, and interference light E2 is generated. The interference light E2 is incident on the detector 140, and is detected by a photodiode or the like within the detector 140.

The detector 140 detects interference light E2 between reference light E(R) and signal light E(S), and derives a refractive index of the measured object 200 based on the detected interference light E2.

The foregoing is description about an operation of the light measurement device 100.

As described above, the light measurement device 100 includes the phase adjustment unit 120 and the detector 140. The phase adjustment unit 120 adjusts the phase difference between signal light E(S) based on object light E1 being light to be obtained by transmission or reflection of light E from a light source with respect to the measured object 200, and reference light E(R) for use in obtaining interference light E2 with respect to the signal light E(S). The detector 140 detects interference light E2 between signal light E(S) and reference light E(R) to be output by the phase adjustment unit 120, and derives a refractive index of the measured object 200 based on the interference light E2. Herein, the detector 140 derives a refractive index of the measured object 200, based on interference light E2 between reference light E(R) after phase adjustment, and signal light E(S) whose phase is not adjusted. Further, the optical axis of light from a light source or object light is linearly disposed, and the phase adjustment unit 120 and the detector 140 are disposed on the optical axis of light E from a light source or object light E1.

In this way, in the light measurement device 100, the optical axis of light from a light source or object light is linearly disposed, and the phase adjustment unit 120 and the detector 140 are disposed on the optical axis of light E from a light source or object light E1. The phase adjustment unit 120 adjusts the phases of reference light E(R) and signal light E(S) by controlling the refractive index of a spatial light modulator, for instance. Therefore, unlike the OCT illustrated in FIG. 8, a mechanical adjustment component for adjusting the optical path length or the like by moving a reference light mirror is not necessary. Thus, in the light measurement device 100, it is possible to obtain signal light E(S) based on object light E1, and reference light E(R) of a phase different from the phase of the signal light E(S) with a simplified configuration, as compared with the OCT illustrated in FIG. 8. Therefore, according to the light measurement device 100, it is possible to derive a refractive index of the measured object 200 with a simplified configuration.

Further, in the light measurement device 100, unlike the OCT illustrated in FIG. 8, a beam splitter or a half mirror for splitting light into two beams is not necessary. This makes it easy to adjust the layout of the components. Therefore, it is easy to obtain interference fringes with high brightness, which leads to improvement of measurement accuracy.

Further, in the light measurement device 100, the entirety of reference light E(R) and signal light E(S) to be output by the phase adjustment unit 120 is used in generation of interference light E2. Therefore, unlike the OCT illustrated in FIG. 8, it is not necessary to use a part of reference light or reflection light. This makes it possible to increase the light intensity of interference light E2 to be detected by the detector 140, as compared with a configuration as exemplified by the OCT illustrated in FIG. 8. Further, it is possible to attain light amount uniformity of reference light E(R) and signal light E(S) by controlling channels and the like of the phase adjustment unit 120.

Further, in the light measurement device 100, unlike the OCT illustrated in FIG. 8, a reference light mirror is not necessary. This makes it easy to adjust the layout of the components. Further, unlike the OCT illustrated in FIG. 8, in the light measurement device 100, a beam splitter or a half mirror is not necessary. This makes it possible to miniaturize the light measurement device 100, as compared with the OCT illustrated in FIG. 8. Further, it is possible to configure the light measurement device 100 with a less number of components, as compared with the OCT illustrated in FIG. 8.

Further, in the light measurement device 100, the phase adjustment unit 120 adjusts the phase difference between reference light E(R) and signal light E(S) by using light E(R) such that the phase of object light E1 is adjusted as reference light, and by using light E(S) whose phase is not adjusted as signal light.

In this way, in the light measurement device 100, the phase adjustment unit 120 adjusts the phase difference between reference light E(R) whose phase is adjusted, and signal light E(S) whose phase is not adjusted. This makes it possible to measure a refractive index of the measured object 200 with a simplified configuration, as well as the aforementioned content.

Further, in the light measurement device 100, the phase adjustment unit 120 includes a spatial light modulator. The spatial light modulator includes a liquid crystal unit, and changes the optical path length of a part of incident light by partially changing the refractive index of the liquid crystal unit. This makes it possible to change the phase of a part of light to be input to the spatial light modulator at the time of output. Consequently, it is easy to produce the light measurement device 100 with use of a spatial light modulator as an existing product.

In the light measurement device 100, it is also possible to form a liquid crystal unit by a micro-optical element. This makes it possible to more finely and more accurately adjust the amount of light transmitting through the liquid crystal unit out of light to be incident on the phase adjustment unit 120. Therefore, it is easy to attain light amount uniformity of two beams to be output by the phase adjustment unit 120 (reference light E(R) after phase adjustment by the phase adjustment unit 120, and signal light E(S) whose phase is not adjusted). Thus, it is possible to increase brightness of interference fringes by interference light E2 to be detected by the detector 140. This makes it possible to enhance measurement accuracy of the light measurement device 100.

Further, in the light measurement device 100, a plurality of phase adjustment units 120, or a phase adjustment unit 120 extending in a columnar shape along an optical axis direction may be arranged in series along the optical axis of light E from a light source between the measured object 200 and the detector 140. This makes it possible to increase a phase difference between reference light and signal light.

Further, in a light measurement device 100 in the first exemplary embodiment of the present invention, a light source (not illustrated) and a detector 140 preferably operate in a visible range. Herein, it is known that the shorter the wavelength is, the larger the phase change amount is. Therefore, using light in a visible range for a light source (not illustrated) and the detector 140 makes it possible to efficiently increase the phase change amount. Consequently, it is possible to obtain a large phase change amount without disposing a plurality of phase adjustment units in series in multiple stages.

First Exemplary Embodiment

Figure 3:
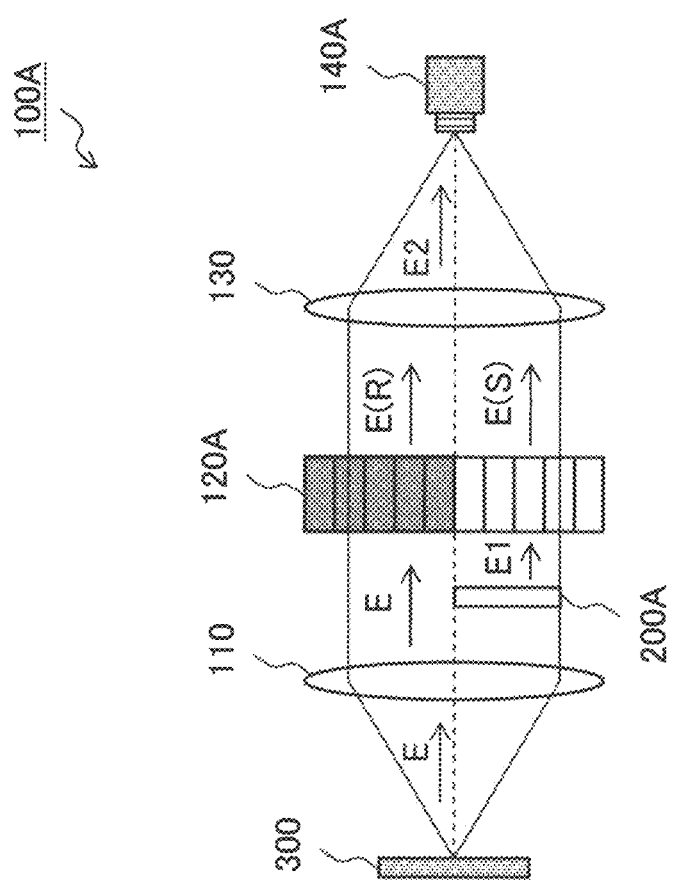
FIG. 3 is a diagram schematically illustrating a configuration of a light measurement device in a first exemplary embodiment of the present invention.

FIG. 3 is a diagram schematically illustrating a configuration of a light measurement device 100A in the first exemplary embodiment of the present invention. Note that in FIG. 3, constituent elements equivalent to the constituent elements illustrated in FIG. 1 and FIG. 2 are indicated by the same reference numerals as the reference numerals illustrated in FIG. 1 and FIG. 2.

As illustrated in FIG. 3, the light measurement device 100A includes a first lens 110, a phase adjustment unit 120A, a second lens 130, and a detector 140A. Note that as will be described later, the first lens 110 and the second lens 130 may be omitted. Specifically, in a case where the beam diameter of light source light E from a light source 300 is sufficiently large to such an extent that the device can function as a phase adjustment unit, as compared with the sectional area of the phase adjustment unit 120A in an optical axis direction, the first lens 110 and the second lens 130 are not essential constituent elements.

As illustrated in FIG. 3, a measured object 200A is disposed between the first lens 110 and the phase adjustment unit 120A, as a measurement object for the light measurement device 100A. Examples of the measured object 200A are a liquid and a living body. The measured object 200A, however, is not limited to the above, as far as the measured object transmits or reflects light.

Herein, comparison is made between FIG. 1 and FIG. 3. FIG. 3 is different from FIG. 1 in a point that the measured object 200A is disposed between the first lens 110 and the phase adjustment unit 120A. In this case, the measured object 200A faces only a lower area (on the lower side on the plane of FIG. 3) of the phase adjustment unit 120A below the center of the phase adjustment unit 120A. Likewise, the measured object 200A faces only a lower area (on the lower side on the plane of FIG. 3) of the first lens 110 with respect to the optical axis of the first lens 110.

As illustrated in FIG. 3, the light source 300 is disposed to face the first lens 110. The light source 300 emits light such as infrared light as light source light E, for instance.

As illustrated in FIG. 3, the first lens 110, the phase adjustment unit 120A, the second lens 130, and the detector 140A are disposed along the optical axis of light source light E. The optical axis of light E from a light source is linearly disposed.

Note that as described above, as light E from a light source, for instance, near infrared light in the range of from about 0.78 μm to 2.5 μm is used. Note that as light E from a light source, it is also possible to use ultraviolet light (in the range of from about 0.01 μm to 0.38 μm), visible light (in the range of from about 0.38 μm to 0.78 μm), mid infrared light (in the range of from about 2.5 μm to 25 μm), or far infrared light (in the range of from about 25 μm to 100 μm) other than the above.

As illustrated in FIG. 3, the first lens 110 is disposed between the light source 300 and the phase adjustment unit 120A. Further, the first lens 110 is disposed on the optical axis of light source light E. Light source light E is incident on the first lens 110. The first lens 110 converts incident light source light E into a parallel light flux. The first lens 110 is made of glass or a resin material.

As illustrated in FIG. 3, the measured object 200A is disposed between a lower area (on the lower side on the plane of FIG. 3) of the first lens 110 with respect to the optical axis of the first lens 110, and a lower area (on the lower side on the plane of FIG. 3) of the phase adjustment unit 120A below the center of the phase adjustment unit 120A. Specifically, the measured object 200A faces only a lower area of the phase adjustment unit 120A below the center of the phase adjustment unit 120A. Likewise, the measured object 200A faces only a lower area of the first lens 110 with respect to the optical axis of the first lens 110. Light source light E is incident on the measured object 200A. Object light E1 being light to be obtained by transmission of light source light E through the measured object 200A is incident on a lower area of the phase adjustment unit 120A below the center of the phase adjustment unit 120A. Note that as will be described later using FIG. 4, providing a mechanism in which light source light E from the first lens 110 is extracted for radiation to the measured object 200A, and reflection light from the measured object 200A is allowed to be incident on the phase adjustment unit 120A also makes it possible to handle reflection light from the measured object 200A.

As illustrated in FIG. 3, the phase adjustment unit 120A is disposed between the first lens 110 and the second lens 130. Further, the phase adjustment unit 120A is disposed on optical axes of light source light E and object light E1. Light source light E as a parallel light flux obtained by conversion by the first lens 110 is incident on an upper area of the phase adjustment unit 120A. Object light E1 being light to be obtained by transmission of light source light E through the measured object 200A is incident on a lower area of the phase adjustment unit 120A. The phase adjustment unit 120A adjusts the phase of object light E1. The phase adjustment unit 120A adjusts the phase difference between signal light and reference light, wherein signal light E(S) is based on object light E1 being light to be obtained by transmission or reflection of light from a light source with respect to the measured object 200, and reference light E(R) is used for obtaining interference light E2 (to be described later) with respect to the signal light E(S).

Herein, the phase adjustment unit 120A generates a phase difference between an upper area of light source light E and a lower area of object light E1 by applying different modulations to the upper area (on the upper side on the plane of FIG. 3) of light source light E above the center of the phase adjustment unit 120A, and the lower area (on the lower side on the plane of FIG. 3) of object light E1 below the center of the phase adjustment unit 120A. Specifically, the phase adjustment unit 120A adjusts the phase of an upper area (on the upper side on the plane of FIG. 3) of incident light source light E above the center of the phase adjustment unit 120A, and does not adjust the phase of a lower area (on the lower side on the plane of FIG. 3) of incident object light E1 below the center of the phase adjustment unit 120A. Therefore, the phase adjustment unit 120A outputs light source light E whose phase is adjusted by the phase adjustment unit 120A from an upper area of the phase adjustment unit 120A as reference light E(R), and outputs object light E1 from a lower area of the phase adjustment unit 120A as signal light E(S). Note that the exemplary embodiment is not limited to the above. The measured object 200A may be disposed on the upper side (on the upper side on the plane of FIG. 3) above the center of light of object light E1. In this case, the phase adjustment unit 120A adjusts the phase of a lower portion (on the lower side on the plane of FIG. 3) of light source light E above the center of the optical path of the light source light E, and may not adjust the phase of an upper portion (on the upper side on the plane of FIG. 3) of object light E1 below the center of the light source light E.

In this case, the phase adjustment unit 120A adjusts and outputs light in such a manner that the light amount of reference light E(R) is equal to the light amount of signal light E(S).

For instance, as the phase adjustment unit 120A, a spatial light modulator (SLM) can two-dimensionally control the phase of light. The spatial light modulator internally includes a liquid crystal unit. The spatial light modulator changes the optical path length of a part of incident light by controlling the refractive index of the liquid crystal unit provided therein. Consequently, the phase of light to be input on the spatial light modulator is adjusted. In this case, the spatial light modulator finely adjusts a channel to be controlled or a channel not to be controlled the spatial light modulator in such a manner that the light amounts of reference light E(R) and signal light E(S) to be output by the phase adjustment unit 120A are equal to each other. Further, positions of the measured object 200A, the first lens 110, the second lens 130, and the detector 140A are also adjusted. Herein, a spatial light modulator imparts a phase shift by a channel to be controlled.

In a case where a spatial light modulator is of a transmission type, the spatial light modulator has features such that the spatial light modulator can dominantly modulate the phase of light, control for each space, obtain a high light use efficiency, miniaturize the device, and is controllable by a simplified computer.

Further, a micro-optical element may be used in place of a liquid crystal unit (not illustrated) of a spatial light modulator. Examples of the micro-optical element are an micro electro mechanical systems (MEMS), a silicon device, and a compound device.

As illustrated in FIG. 3, the second lens 130 is disposed between the phase adjustment unit 120A and the detector 140. The second lens 130 collects reference light E(R) and signal light E(S) to be output from the phase adjustment unit 120A.

According to the aforementioned configuration, it is possible to detect, by the detector 140A, light (interference light E2) generated by interference between reference light E(R) and signal light E(S) to be output by the phase adjustment unit 120. Specifically, interference light E2 is generated by interference between reference light E(R) and signal light E(S) to be output by the phase adjustment unit 120A. The interference light E2 is incident on the detector 140A.

As illustrated in FIG. 3, the detector 140A is disposed to face the second lens 130. The detector 140A is disposed on the optical axis of light E from the light source 300. Interference light E2 formed by the second lens 130 is incident on the detector 140A. More specifically, interference light E2 between reference light E(R) and signal light E(S) is incident on the detector 140A.

The detector 140A detects interference light E2 between reference light E(R) and signal light E(S) to be output by the phase adjustment unit 120A, and acquires a light intensity distribution of the measured object 200A in an optical axis direction, based on the detected interference light E2. The detector 140A includes a light receiving element, for instance.

Next, an operation of the light measurement device 100A is described.

As well as the content described using FIG. 2, positions of the first lens 110, the phase adjustment unit 120A, the second lens 130, and the detector 140A are adjusted. In this way, controlling optical axis adjustment and the amount of light for splitting independently of each other makes it easy to attain light amount uniformity of two beams (reference light E(R) and signal light E(S)). Therefore, it is possible to increase brightness of interference fringes by interference light E2 to be detected by the detector 140A.

First of all, light from the light source 300 is incident on the first lens 110. The first lens 110 converts incident light source light E into a parallel light flux. An upper portion of light source light E, which is converted into a parallel light flux by the first lens 110, is incident on an upper portion of the phase adjustment unit 120A. Herein, a lower portion of light source light E, which is converted into a parallel light flux by the first lens 110, is incident on the measured object 200A by disposing the measured object 200A on the lower side.

When light source light E transmits through the measured object 200A, object light E1 is generated. The object light E1 is incident on a lower portion of the phase adjustment unit 120A.

The phase adjustment unit 120A adjusts the phase of light source light E to be incident on an upper portion (on the upper side on the plane of FIG. 3) of the phase adjustment unit 120A. On the other hand, the phase adjustment unit 120 does not adjust the phase of object light E1 to be incident on a lower portion (on the lower side on the plane of FIG. 3) of the phase adjustment unit 120A.

The phase adjustment unit 120A outputs reference light E(R) after phase adjustment from an upper area of the phase adjustment unit 120A toward the second lens 130, and outputs signal light E(S) whose phase is not adjusted from a lower area of the phase adjustment unit 120A toward the second lens 130.

Reference light E(R) and signal light E(S) output by the phase adjustment unit 120A are incident on the second lens 130.

Next, the second lens 130 collects reference light E(R) and signal light E(S) to be output from the phase adjustment unit 120A. Specifically, the second lens 130 collects reference light E(R) after phase adjustment by the phase adjustment unit 120A, and signal light E(S) whose phase is not adjusted. Then, signal light E(S) and reference light E(R) to be output by the phase adjustment unit 120A interfere with each other. Specifically, reference light E(R) and signal light E(S) to be output by the phase adjustment unit 120A interfere with each other, and interference light E2 is generated.

The interference light E2 is incident on the detector 140A, and is detected by a photodiode or the like within the detector 140A.

The detector 140A acquires a light intensity distribution of the measured object 200A in an optical axis direction, based on interference light E2 between reference light E(R) and signal light E(S).

The foregoing is description about an operation of the light measurement device 100A.

Figure 4:
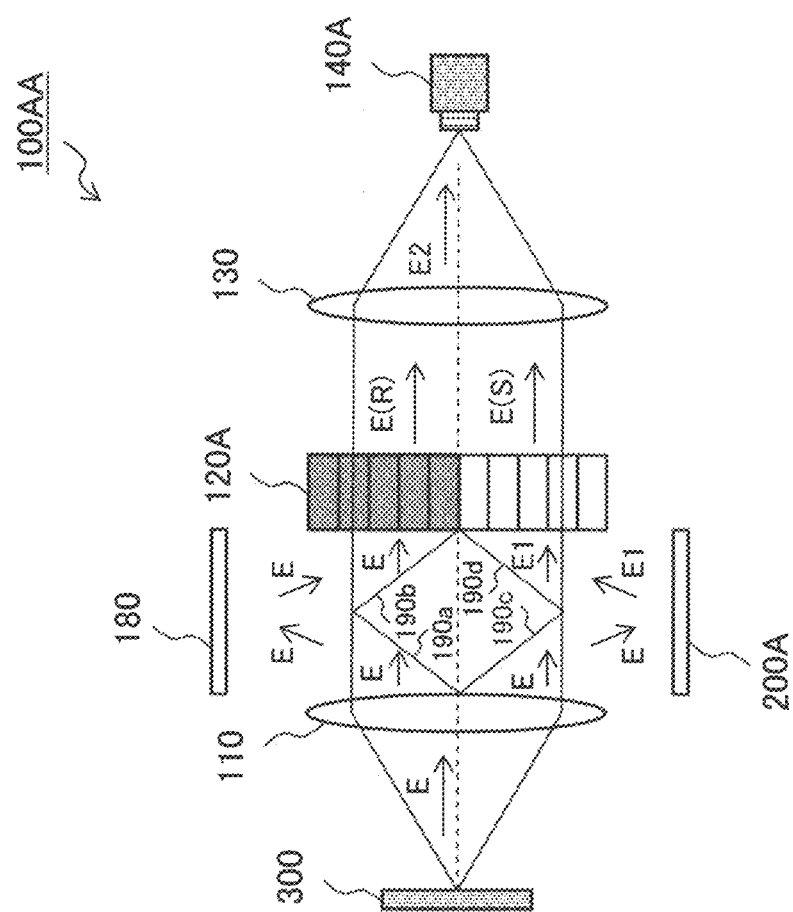
FIG. 4 is a diagram schematically illustrating a configuration of a modification example of the light measurement device in the first exemplary embodiment of the present invention.

Next, a configuration of a light measurement device 100AA as a modification example of the light measurement device 100A in the first exemplary embodiment of the present invention is described. FIG. 4 is a diagram schematically illustrating a configuration of the light measurement device 100AA. Note that in FIG. 4, constituent elements equivalent to the constituent elements illustrated in FIG. 1 to FIG. 3 are indicated by the same reference numerals as the reference numerals illustrated in FIG. 1 to FIG. 3.

As illustrated in FIG. 4, the light measurement device 100AA includes a first lens 110, a phase adjustment unit 120A, a second lens 130, a detector 140A, an outer mirror 180, and inner mirrors 190a to 190d. Note that as will be described later, the first lens 110 and the second lens 130 may be omitted. Specifically, in a case where the beam diameter of light source light E from a light source 300 is sufficiently large to such an extent that the device can function as a phase adjustment unit, as compared with the sectional area of the phase adjustment unit 120A in an optical axis direction, the first lens 110 and the second lens 130 are not essential constituent elements.

As illustrated in FIG. 4, a measured object 200A as a measurement object for the light measurement device 100AA is disposed between the first lens 110 and the phase adjustment unit 120A, and on the lower side of the first lens 110 and the phase adjustment unit 120A.

Herein, comparison is made between FIG. 3 and FIG. 4. In FIG. 3, the measured object 200A is disposed between the first lens 110 and the phase adjustment unit 120A. On the other hand, in FIG. 4, the measured object 200A is disposed between the first lens 110 and the phase adjustment unit 120A, and on the lower side of the first lens 110 and the phase adjustment unit 120A. In this point, FIG. 3 and FIG. 4 are different from each other. In this case, in FIG. 4, the measured object 200A does not face both of the first lens 110 and the phase adjustment unit 120A.

Further, FIG. 4 is different from FIG. 3 in a point that the outer mirror 180 and the inner mirrors 190a to 190d are provided.

In the following, each configuration illustrated in FIG. 4 is described. Note that description on a configuration that are superimposed that in FIG. 3 is simplified or omitted.

As illustrated in FIG. 4, the first lens 110, the phase adjustment unit 120A, the second lens 130, and the detector 140A are disposed along the optical axis of light source light E. The optical axis of light source light E is linearly disposed.

As illustrated in FIG. 4, the outer mirror 180 is disposed between the first lens 110 and the phase adjustment unit 120A, and on the upper side of the first lens 110 and the phase adjustment unit 120A. Further, the outer mirror 180 and the measured object 200A are disposed to face each other. The outer mirror 180 is disposed to face the inner mirrors 190a and 190b. Light source light E to be reflected by the inner mirror 190a is incident on the outer mirror 180. Further, the outer mirror 180 outputs light source light E reflected by the mirror 190a toward the inner mirror 190b.

As illustrated in FIG. 4, the inner mirrors 190a to 190d are disposed between the first lens 110 and the phase adjustment unit 120A. The inner mirrors 190a and 190c split light source light E to be output by the first lens 110. More specifically, the inner mirror 190a reflects incident light source light E in a direction of the outer mirror 180. The inner mirror 190b outputs light E that returns to the inner mirror 190b by reflection on the outer mirror 180 in a direction of the phase adjustment unit 120A. Further, the inner mirror 190c reflects incident light source light E in a direction of the measured object 200A. The inner mirror 190d outputs light E1 that returns to the inner mirror 190d by reflection on the measured object 200A in a direction of the phase adjustment unit 120A.

Object light E1 output by the first lens 110 is incident on an upper area of the phase adjustment unit 120A via the outer mirror 180 and the inner mirrors 190a and 190b. Further, object light E1 being light to be obtained by reflection of light source light E on the measured object 200A is incident on a lower area of the phase adjustment unit 120A via the inner mirrors 190c and 190d. The phase adjustment unit 120A adjusts the phase of object light E1. The phase adjustment unit 120A adjusts the phase difference between signal light E(S) based on object light E1 being light to be obtained by reflection of light from a light source on the measured object 200, and reference light E(R) for use in obtaining interference light E2 with respect to the signal light E(S).

The foregoing is description about a configuration of the light measurement device 100AA.

Next, an operation of the light measurement device 100AA is described.

First of all, light from the light source 300 is incident on the first lens 110. The first lens 110 converts incident light source light E into a parallel light flux. An upper portion of light source light E, which is converted into a parallel light flux by the first lens 110, is reflected by the inner mirror 190a, and propagates toward the outer mirror 180. After light source light E incident on the outer mirror 180 is reflected by the outer mirror 180, the light source light E is incident on an upper portion of the phase adjustment unit 120A via the inner mirror 190b.

A lower portion of light source light E, which is converted into a parallel light flux by the first lens 110, is reflected by the inner mirror 190c, and propagates toward the measured object 200A.

When light source light E is reflected by the measured object 200A, object light E1 is generated. The object light E1 is incident on a lower portion of the phase adjustment unit 120A via the inner mirror 190d.

The phase adjustment unit 120A adjusts the phase of light source light E to be incident on an upper portion (on the upper side on the plane of FIG. 4) of the phase adjustment unit 120A. On the other hand, the phase adjustment unit 120 does not adjust the phase of object light E1 to be incident on a lower portion (on the lower side on the plane of FIG. 4) of the phase adjustment unit 120A.

The phase adjustment unit 120A outputs reference light E(R) after phase adjustment from an upper area of the phase adjustment unit 120A toward the second lens 130, and outputs signal light E(S) whose phase is not adjusted from a lower area of the phase adjustment unit 120A toward the second lens 130.

Operations thereafter are the same as described using FIG. 3.

The foregoing is description about an operation of the light measurement device 100AA.

Herein, as exemplified in FIG. 4, in a case where reflection light is handled, for instance, when signal light E(S) being reflection light of the measured object 200A, and reference light E(R) after adjustment by the phase adjustment unit 120A are optically equidistant, the signal light E(S) and the reference light E(R) interfere with each other, and the detector 140A obtains interference light E2 between the signal light E(S) and the reference light E(R).

Next, in order to obtain interference light E2 from a different position of the measured object 200A, the phase of light source light to be incident on an upper portion of the phase adjustment unit 120A is adjusted in such a manner that the light source light and the object light E1 from a reflection point at the different position are optically equidistant. In this way, causing the detector 140A to detect interference light E2 while sequentially adjusting the phase imparted by the phase adjustment unit 120A makes it possible to obtain a reflection light intensity distribution of the measured object 200A in an optical axis direction.

As described above, the light measurement devices 100A and 100AA in the first example embodiment of the present invention include the phase adjustment unit 120A and the detector 140A. The phase adjustment unit 120 adjusts the phase difference between signal light E(S) based on object light E1 being light to be obtained by transmission or reflection of light E from a light source with respect to the measured object 200, and reference light E(R) for use in obtaining interference light E2 with respect to the signal light E(S). The detector 140A detects interference light E2 between signal light E(S) and reference light E(R) to be output by the phase adjustment unit 120A, and derives a reflection light intensity distribution of the measured object 200A, based on the interference light E2. Herein, the detector 140A derives a reflection light intensity distribution of the measured object 200A, based on interference light E2 between reference light E(R) after phase adjustment, and signal light E(S) whose phase is not adjusted. Further, the optical axis of light from a light source or object light is linearly disposed, and the phase adjustment unit 120A and the detector 140A are disposed on the optical axis of light E from a light source or object light E1.

In this way, in the light measurement devices 100A and 100AA, the optical axis of light from a light source or object light is linearly disposed, and the phase adjustment unit 120A and the detector 140A are disposed on the optical axis of light E from a light source or object light E1. The phase adjustment unit 120A adjusts the phases of reference light E(R) and signal light E(S) by controlling the refractive index of a spatial light modulator, for instance. Therefore, unlike the OCT illustrated in FIG. 8, a mechanical adjustment component for adjusting the optical path length or the like by moving a reference light mirror is not necessary. Thus, in the light measurement devices 100A and 100AA, it is possible to obtain signal light E(S), and reference light E(R) of a phase different from the phase of the signal light E(S) by a more simplified configuration and method, as compared with the OCT illustrated in FIG. 8.

Therefore, according to the light measurement device 100 in the first exemplary embodiment of the present invention, it is possible to derive a reflection light intensity distribution of the measured object 200 with a simplified configuration.

Further, in the light measurement device 100A in the first exemplary embodiment of the present invention, unlike the OCT illustrated in FIG. 8, a beam splitter or a half mirror for splitting light into two beams is not necessary. This makes it easy to adjust the layout of the components. Therefore, it is easy to obtain interference fringes with high brightness, which leads to improvement of measurement accuracy.

Further, in the light measurement devices 100A and 100AA in the first exemplary embodiment of the present invention, the entirety of reference light E(R) and signal light E(S) to be output by the phase adjustment unit 120A is used in generation of interference light E2. Therefore, unlike the OCT illustrated in FIG. 8, it is unnecessary not to use a part of reference light or reflection light. This makes it possible to increase the reflection light intensity of interference light E2 to be detected by the detector 140A, as compared with a configuration as exemplified by the OCT illustrated in FIG. 8. Further, it is possible to attain light amount uniformity by controlling channels and the like of the phase adjustment unit 120A.

Further, in the light measurement device 100A in the first exemplary embodiment of the present invention, unlike the OCT illustrated in FIG. 8, a reference light mirror is not necessary. Therefore, it is easy to adjust the layout of the components. Further, unlike the OCT illustrated in FIG. 8, in the light measurement device 100A, a beam splitter or a half mirror is not necessary. This makes it possible to miniaturize the light measurement device 100A, as compared with the OCT illustrated in FIG. 8. Further, it is possible to configure the light measurement device 100A with a less number of components, as compared with the OCT illustrated in FIG. 8.

Further, in the light measurement devices 100A and 100AA in the first exemplary embodiment of the present invention, the phase adjustment unit 120A includes a spatial light modulator. The spatial light modulator includes a liquid crystal unit, and changes the optical path length of a part of incident light by partially changing the refractive index of the liquid crystal unit. This makes it possible to change the phase of a part of light to be input to the spatial light modulator at the time of output. Consequently, it is easy to produce the light measurement devices 100A and 100AA with use of an existing spatial light modulator product.

Further, in the light measurement devices 100A and 100AA in the first exemplary embodiment of the present invention, it is also possible to form a liquid crystal unit by a micro-optical element. This makes it possible to more finely and more accurately adjust the amount of light transmitting through the liquid crystal unit out of light to be incident on the phase adjustment unit 120A. Therefore, it is easy to attain light amount uniformity of two beams to be output by the phase adjustment unit 120A (reference light E(R) and signal light E(S) to be output by the phase adjustment unit 120A). Thus, it is possible to increase brightness of interference fringes by interference light E2 to be detected by the detector 140A. This makes it possible to enhance measurement accuracy of the light measurement devices 100A and 100AA.

Further, in the light measurement devices 100A and 100AA in the first exemplary embodiment of the present invention, a plurality of phase adjustment units 120A, or a phase adjustment unit 120A extending in a columnar shape along an optical axis direction may be disposed in series along the optical axis of light E from a light source between the measured object 200A and the detector 140A. This makes it possible to increase the phase difference between reference light E(R) and signal light E(S).

Further, in the light measurement devices 100A and 100AA in the first exemplary embodiment of the present invention, a light source (not illustrated) and the detector 140A preferably operate in a visible range. Herein, it is known that the shorter the wavelength is, the larger the phase change amount is. Therefore, using light in a visible range and a detector capable of detecting light in a visible range as a light source (not illustrated) and the detector 140A makes it possible to efficiently increase the phase change amount. Consequently, it is also possible to obtain a large phase change amount without disposing a plurality of phase adjustment units in series in multiple stages. It is needless to say that ultraviolet light, near infrared light, mid infrared light, or far infrared light may be used as described above. In the light measurement devices 100A and 100AA in the first exemplary embodiment of the present invention, the phase adjustment unit 120A adjusts the phase difference between signal light E(S) and reference light E(R) by using light such that the phase of light source light E is adjusted as the reference light E(R), and by using light such that the phase of object light E1 is not adjusted as the signal light E(S). The detector 140A acquires a reflection light intensity distribution of the measured object 200A, based on interference light E2 between signal light E(S) and reference light E(R).

In this way, in the light measurement devices 100A and 100AA, the phase adjustment unit 120A adjusts the phase difference between signal light E(S) and reference light E(R) by using light such that the phase of light source light E is adjusted by the phase adjustment unit 120A as the reference light E(R), and by using light such that the phase of object light E1 is not adjusted as the signal light E(S). This makes it possible to measure a reflection light intensity distribution of the measured object 200A in an optical axis direction.

Second Exemplary Embodiment

FIG. 5 is a diagram schematically illustrating a configuration of a light measurement device 100B in the second exemplary embodiment of the present invention. Note that in FIG. 5, constituent elements equivalent to the constituent elements illustrated in FIG. 1 to FIG. 4 are indicated by the same reference numerals as the reference numerals illustrated in FIG. 1 to FIG. 4.

As illustrated in FIG. 5, the light measurement device 100B includes a first lens 110, a phase adjustment unit 120B, a second lens 130, and a detector 140B. Note that the first lens 110 and the second lens 130 may be omitted as well as the content described using FIG. 1.

As illustrated in FIG. 5, a measured object 200B is disposed between the first lens 110 and the phase adjustment unit 120B as a measurement object for the light measurement device 100B. Examples of the measured object 200B are a liquid and a living body. The measured object 200B, however, is not limited to the above, as far as the measured object transmits or reflects light.

Herein, comparison is made between FIG. 3 and FIG. 5. FIG. 5 is different from FIG. 3 in a point that excitation light ER is incident on the measured object 200B.

As illustrated in FIG. 5, the first lens 110, the phase adjustment unit 120B, the second lens 130, and the detector 140B are disposed along the optical axis of light source light E.

As illustrated in FIG. 5, the measured object 200B is disposed between a lower portion (on the lower side on the plane of FIG. 5) of the first lens 110 with respect to the optical axis of the first lens 110, and a lower portion (on the lower side on the plane of FIG. 5) of the phase adjustment unit 120B below the center of the phase adjustment unit 120B. Specifically, the measured object 200B faces only a lower portion of the phase adjustment unit 120B. Likewise, the measured object 200B faces only a lower portion of the first lens 110. Light source light E and excitation light ER are incident on the measured object 200B. Allowing incidence of excitation light ER on the measured object 200B makes it possible to change the refractive index of the measured object 200B.

As excitation light ER, ultraviolet light, visible light, or X-ray is used, for instance. When excitation light ER is incident on the measured object 200B, the measured object 200B absorbs energy of the excitation light ER and turns to an excited state, and the refractive index of the measured object 200B also changes. Excitation object light E4 being light to be obtained by transmission or reflection of light source light E and excitation light ER with respect to the measured object 200A is incident on a lower portion of the phase adjustment unit 120A.

As illustrated in FIG. 5, the phase adjustment unit 120B is disposed between the first lens 110 and the second lens 130. Further, the phase adjustment unit 120B is disposed on the optical axes of light source light E and excitation object light E4. Light source light E, which is converted into a parallel light flux by the first lens 110, is incident on an upper area of the phase adjustment unit 120B. Excitation object light E4 being light to be obtained by transmission or reflection of light source light E and excitation light ER with respect to the measured object 200A is incident on a lower area of the phase adjustment unit 120B. The phase adjustment unit 120B adjusts the phase of incident light.

The phase adjustment unit 120B adjusts the phase difference between signal light E(S) and reference light E(R) by using excitation object light E4 being light to be obtained by transmission or reflection of light source light E and excitation light ER with respect to the measured object 200B as the signal light E(S), and by using light whose phase is adjusted with respect to the light source light E as the reference light E(R).

Herein, the phase adjustment unit 120B generates a phase difference between light source light E and excitation object light E4 by applying different modulations to an upper area (on the upper side on the plane of FIG. 5) of the light source light E above the center of the phase adjustment unit 120B, and to a lower area (on the lower side on the plane of FIG. 5) of the excitation object light E4 below the center of the phase adjustment unit 120B. Specifically, the phase adjustment unit 120B adjusts the phase of an upper area (on the upper side on the plane of FIG. 5) of incident light source light E above the center of the phase adjustment unit 120B, and does not adjust the phase of a lower area (on the lower side on the plane of FIG. 5) of incident excitation object light E4 below the center of the phase adjustment unit 120B. Therefore, the phase adjustment unit 120B outputs light source light E after phase adjustment by the phase adjustment unit 120A from an upper area of the phase adjustment unit 120B as reference light E(R), and outputs excitation object light E4 as signal light E(S).

Note that the exemplary embodiment is not limited to the above. The measured object 200B may be disposed on the upper side (on the upper side on the plane of FIG. 5) above the center of light source light E. In this case, the phase adjustment unit 120B may adjust the phase of a lower portion (on the lower side on the plane of FIG. 5) of light source light E below the center of the optical path of the light source light E, and may not adjust the phase of an upper portion (on the upper side on the plane of FIG. 5) of excitation object light E4 above the center of the light source light E.

In this case, the phase adjustment unit 120B adjusts and outputs light in such a manner that the light amount of reference light E(R) is equal to the light amount of signal light E(S). Note that as well as the phase adjustment unit 120A described in the first exemplary embodiment, the phase adjustment unit 120B includes a spatial light modulator, for instance. Details on the spatial light modulator are the same as the content described in the first exemplary embodiment.

As illustrated in FIG. 5, the second lens 130 is disposed between the phase adjustment unit 120B and the detector 140B. The second lens 130 collects reference light E(R) and signal light E(S) to be output from the phase adjustment unit 120B. According to the aforementioned configuration, it is possible to detect, by the detector 140B, light (interference light E2) generated by interference between reference light E(R) and signal light E(S) to be output by the phase adjustment unit 120B.

Specifically, interference light E2 is generated by interference between reference light E(R) and signal light E(S) to be output by the phase adjustment unit 120B. The interference light E2 is incident on the detector 140B.

As illustrated in FIG. 5, the detector 140B is disposed to face the second lens 130. The detector 140B is disposed on the optical axis of light source light E. Interference light E2 formed by the second lens 130 is incident on the detector 140B. More specifically, interference light E2 between reference light E(R) and signal light E(S) is incident on the detector 140B.

The detector 140B detects interference light E2 between reference light E(R) and signal light E(S) to be output by the phase adjustment unit 120B, and derives a change in the refractive index of the measured object 200B, based on detected interference light E2. The detector 140B includes a spectral measurement device. The spectral measurement device detects a light intensity in a spectral domain of interference light E2.

Next, an operation of the light measurement device 100B is described.

As in the content described using FIG. 2, positions of the first lens 110, the phase adjustment unit 120B, the second lens 130, and the detector 140B are adjusted. In this way, controlling optical axis adjustment and the amount of light for splitting independently of each other makes it easy to attain light amount uniformity of two beams (signal light and reference light). Therefore, it is possible to increase brightness of interference fringes in a spectral domain by interference light E2 to be detected by the detector 140B.

First of all, light from a light source 300 is incident on the first lens 110. The first lens 110 converts incident light source light E into a parallel light flux. An upper portion of light source light E, which is converted into a parallel light flux by the first lens 110, is incident on an upper portion of the phase adjustment unit 120B. A lower portion of light source light E, which is converted into a parallel light flux by the first lens 110, is incident on the measured object 200B. Note that the measured object 200B in an excited state by excitation light ER immediately returns to a ground state. In view of the above, it is general to use a light source for outputting an ultrashort light pulse, as the light source 300.

Next, as illustrated in FIG. 5, light source light E and excitation light ER are incident on the measured object 200A. Allowing incidence of excitation light ER on the measured object 200B makes it possible to change the refractive index of the measured object 200B.

When light source light E and excitation light ER transmit or reflect with respect to the measured object 200A, excitation object light E4 is generated. The excitation object light E4 is incident on a lower portion of the phase adjustment unit 120B.

The phase adjustment unit 120B adjusts the phase of light source light E to be incident on an upper portion (on the upper side on the plane of FIG. 5) of the phase adjustment unit 120B. On the other hand, the phase adjustment unit 120B does not adjust the phase of excitation object light E4 to be incident on a lower portion (on the lower side on the plane of FIG. 5) of the phase adjustment unit 120B.

Next, the phase adjustment unit 120B outputs reference light E(R) after phase adjustment from an upper area of the phase adjustment unit 120B toward the second lens 130, and outputs signal light E(S) whose phase is not adjusted from a lower area of the phase adjustment unit 120B toward the second lens 130.

Reference light E(R) and signal light E(S) output by the phase adjustment unit 120B are incident on the second lens 130.

Next, the second lens 130 collects signal light E(S) and reference light E(R) to be output from the phase adjustment unit 120B. Specifically, the second lens 130 collects reference light E(R) after phase adjustment by the phase adjustment unit 120B, and signal light E(S) whose phase is not adjusted. Then, signal light E(S) and reference light E(R) to be output by the phase adjustment unit 120A interfere with each other.

Specifically, reference light E(R) whose phase is adjusted by the phase adjustment unit 120B, and signal light E(S) interfere with each other, and interference light E2 is generated.

The interference light E2 is incident on the detector 140B. The detector 140B derives a change in the refractive index of the measured object 200B, based on interference light E2 between signal light E(S) and reference light E(R). In this case, the detector 140B detects interference fringes in a spectral domain, which are generated by interference light E2, and derives a change in the refractive index, which is generated in the measured object 200B from a difference in spectral interference fringes due to the presence or absence of incidence of excitation light ER.

The foregoing is description about an operation of the light measurement device 100B.

Note that in the foregoing description, the phase adjustment unit 120A adjusts the phase of incident light source light E in an upper area (on the upper side on the plane of FIG. 5) of the phase adjustment unit 120A, and does not adjust the phase of incident excitation object light E4 in a lower area (on the lower side on the plane of FIG. 5) of the phase adjustment unit 120A. Alternatively, the phase adjustment unit 120B may output signal light E(S) and reference light E(R) by using light E4 whose phase is adjusted with respect to excitation object light E4 being light to be obtained by transmission or reflection of light E from the light source 300 and excitation light ER with respect to the measured object 200B as the signal light E(S), and by using the light E from the light source 300 as the reference light E(R). This also makes it possible to provide the same advantageous effects as the foregoing content.

As described above, in the light measurement device 100B in the third exemplary embodiment of the present invention, excitation light ER is incident on the measured object 200B. Further, the phase adjustment unit 120B adjusts the phase difference between signal light E(S) and reference light E(R) by using excitation object light E4 being light to be obtained by transmission or reflection of light E from the light source 300 and excitation light ER with respect to the measured object 200B as the signal light E(S), and by using light whose phase is adjusted with respect to the light E from the light source 300 as the reference light E(R). The detector 140B is a spectral measurement device configured to derive a change in the refractive index of the measured object 200B, based on interference light E2 between signal light E(S) and reference light E(R).

In this way, in the light measurement device 100B, the phase adjustment unit 120B adjusts the phase difference between signal light E(S) and reference light E(R) by using excitation object light E4 being light to be obtained by transmission or reflection of light E from the light source 300 and excitation light ER with respect to the measured object 200B as the signal light E(S), and by using light source light E after phase adjustment as the reference light E(R). This makes it possible to measure a change in the refractive index of the measured object 200B. In this case, in the light measurement device 100B, excitation light ER is incident on the measured object 200B. Therefore, it is possible to change the refractive index of the measured object 200B by excitation light ER. This makes it possible to change the phase of the optical path of light to be output from the measured object 200B, and to change interference fringes in a spectral domain based on interference light E2. Consequently, the detector 140B as a spectral measurement device can detect a change in the refractive index of the measured object 200B from a change in spectral interference fringes.

Third Exemplary Embodiment

FIG. 6 is a diagram schematically illustrating a configuration of a light measurement device 100C in the third exemplary embodiment of the present invention. Note that in FIG. 6, constituent elements equivalent to the constituent elements illustrated in FIG. 1 to FIG. 5 are indicated by the same reference numerals as the reference numerals illustrated in FIG. 1 to FIG. 5.

As illustrated in FIG. 6, the light measurement device 100C includes a first lens 110, a phase adjustment unit 120C, a second lens 130, a non-linear optical crystal 150, and a detector 140C. Note that as in the content described using FIG. 1, the first lens 110 and the second lens 130 may be omitted.

As illustrated in FIG. 6, a measured object 200C is disposed on the front side of the first lens 110, as a measurement object for the light measurement device 100C. Examples of the measured object 200C are a liquid and a living body. The measured object 200C, however, is not limited to the above, as far as the measured object transmits or reflects light.

Herein, comparison is made between FIG. 1 and FIG. 6. FIG. 6 is different from FIG. 1 in a point that the non-linear optical crystal 150 is disposed between the second lens 130 and the detector 140C. Further, a distributed pulse PD is incident on the non-linear optical crystal 150.

As illustrated in FIG. 6, the first lens 110, the phase adjustment unit 120C, the second lens 130, the non-linear optical crystal 150, and the detector 140C are disposed along the optical axis of pulsed light PL as light source light. Further, the optical axis of pulsed object light E6 to be described later is linearly disposed.

As illustrated in FIG. 6, pulsed light PL is incident on the measured object 200C as light source light. Further, pulsed object light E6 being light to be obtained by transmission or reflection of pulsed light PL with respect to the measured object 200C is output from the measured object 200C. Note that it is general to use a light source for outputting an ultrashort light pulse for generating pulsed light PL. Allowing incidence of pulsed light PL on the measured object 200C makes it possible to cause non-linear interaction.

As illustrated in FIG. 6, the phase adjustment unit 120C is disposed between the first lens 110 and the second lens 130. Further, the phase adjustment unit 120C is disposed on the optical axis of pulsed object light E6. Pulsed object light E6, which is converted into a parallel light flux by the first lens 110, is incident on both of an upper area (on the upper side on the plane of FIG. 6) and a lower area (on the lower side on the plane of FIG. 6) of the phase adjustment unit 120C. The phase adjustment unit 120C adjusts the phase of a part of incident light.

The phase adjustment unit 120C adjusts the phase difference between signal light E(S) and reference light E(R) by using pulsed object light E6 being light to be obtained by transmission or reflection of pulsed light PL with respect to the measured object 200C as the signal light E(S), and by using light, which is the pulsed light E6 whose phase is adjusted, as the reference light E(R).

Herein, the phase adjustment unit 120C generates a phase difference between an upper portion of object light E6 and a lower portion of pulsed object light E6 by applying different modulations to an upper portion (on the upper side on the plane of FIG. 6) of the object light E6 with respect to the center of the phase adjustment unit 120C, and to a lower portion (on the lower side on the plane of FIG. 6) of the pulsed object light E6 with respect to the center of the phase adjustment unit 120C. For instance, the phase adjustment unit 120C may generate a phase difference by modulating both of an upper portion (on the upper side on the plane of FIG. 6) of pulsed object light E6 with respect to the center of the phase adjustment unit 120C, and a lower portion (on the lower side on the plane of FIG. 6) of the pulsed object light E6 with respect to the center of the phase adjustment unit 120C. Alternatively, the phase adjustment unit 120C may adjust the phase of an upper portion (on the upper side on the plane of FIG. 6) of pulsed object light E6 with respect to the center of the phase adjustment unit 120C by modulating only the upper portion (on the upper side on the plane of FIG. 6) of the pulsed object light E6 with respect to the center of the phase adjustment unit 120C, and may not adjust the phase of a lower portion (on the lower side on the plane of FIG. 6) of the pulsed object light E6 with respect to the center of the phase adjustment unit 120C.

Note that the exemplary embodiment is not limited to the above. The phase adjustment unit 120C may adjust the phase of a lower portion (on the lower side on the plane of FIG. 6) of object light E6 with respect to the center of the optical path of pulsed object light E6, and may not adjust the phase of an upper portion (on the upper side on the plane of FIG. 6) of the pulsed object light E6 with respect to the center of the optical path of the pulsed object light E6. In a case where the phase adjustment unit 120C modulates only an upper portion (on the upper side on the plane of FIG. 6) of pulsed object light E6 or a lower portion (on the lower side on the plane of FIG. 6) of the pulsed object light E6 with respect to the center of the phase adjustment unit 120C, for instance, the phase adjustment unit 120C outputs signal light E(S) as follows. Specifically, in this case, the phase adjustment unit 120C outputs object light after phase adjustment by the phase adjustment unit 120C as reference light E(R), and outputs object light whose phase is not adjusted by the phase adjustment unit 120C as signal light E(S).

In this case, the phase adjustment unit 120C adjusts and outputs light in such a manner that the light amount of reference light E(R) after phase adjustment by the phase adjustment unit 120C is equal to the light amount of signal light E(S) whose phase is not adjusted. Note that as well as the phase adjustment unit 120A described in the first exemplary embodiment, the phase adjustment unit 120C includes a spatial light modulator, for instance. Details on the spatial light modulator are the same as the content described in the first exemplary embodiment.

As illustrated in FIG. 6, the second lens 130 is disposed between the phase adjustment unit 120C and the non-linear optical crystal 150. The second lens 130 is disposed on the optical axis of pulsed object light E6. The second lens 130 collects reference light E(R) and signal light E(S) to be output from the phase adjustment unit 120C. Specifically, the second lens 130 collects reference light E(R) after phase adjustment by the phase adjustment unit 120C, and signal light E(S) whose phase is not adjusted.

According to the aforementioned configuration, it is possible to detect, by the detector 140C, light (interference light E2) generated by interference between reference light E(R) and signal light E(S) to be output by the phase adjustment unit 120C. Specifically, interference light E2 is generated by interference between reference light E(R) after phase adjustment by the phase adjustment unit 120C, and signal light E(S) whose phase is not adjusted. The interference light E2 is incident on the non-linear optical crystal 150.

As illustrated in FIG. 6, the non-linear optical crystal 150 is disposed between the second lens 130 and the detector 140C. Interference light E2 is incident on the non-linear optical crystal 150. Further, a distributed pulse PD is also incident on the non-linear optical crystal 150. Thus, a sum frequency C8 is generated (C8).

Note that generation of a sum frequency C8 is based on secondary non-linear optical effects. Specifically, generation of a sum frequency C8 is, for example, results in generation of a polarization wave of ($\omega 1+\omega 2$) being a sum of frequencies of two beams in a case where the two beams respectively having frequencies $\omega 1$ and $\omega 2$ are incident on a non-linear optical crystal.

More specifically, interference light E2 between reference light E(R) after phase adjustment by the phase adjustment unit 120C, and signal light E(S) whose phase is not adjusted is incident on the non-linear optical crystal 150. In addition to the above, when a distributed pulse PD is further incident on the non-linear optical crystal 150, a sum frequency being a sum of a frequency of reference light E(R) after phase adjustment and a frequency of a distributed pulse PD, and a sum frequency being a sum of a frequency of signal light E(S) whose phase is not adjusted and a frequency of a distributed pulse PD are generated.

Herein, the central frequency of the distributed pulse PD changes with time, and the duration time of the distributed pulse PD is increased by allowing the distributed pulse PD to pass through a dispersion medium in advance. The phase of reference light E(R) is adjusted. Therefore, the incident time of reference light E(R) with respect to the non-linear optical crystal 150 is different from that of signal light E(S). Consequently, reference light E(R) and signal light E(S) are superimposed at different times with respect to the distributed pulse PD, whose central frequency changes with time, and whose duration time is sufficiently long.

As described above, instantaneous frequencies of the distributed pulse PD when reference light E(R) and signal light E(S) are superimposed the distributed pulse PD are different from each other. Therefore, two sum frequencies C8 whose frequencies are different from each other are generated. The two sum frequencies C8 are incident on the detector 140C.

As illustrated in FIG. 6, the detector 140C is disposed at a position where the detector 140C can detect generation of a sum frequency at the non-linear optical crystal 150. The detector 140C is disposed on the optical axis of pulsed object light E6. The sum frequency C8 generated by the non-linear optical crystal 150 is input to the detector 140C.

Herein, phase information of pulsed object light E6 is reflected in a spectral component of a sum frequency C8 at the time of generation. Times when reference light E(R) and signal light E(S) are superimposed the distributed pulse PD on the non-linear optical crystal 150 are different from each other. Therefore, instantaneous frequencies of the distributed pulse PD at respective are superimposed points are also different. Consequently, phase information pieces of respective sum frequency spectral components are also different from each other, and two sum frequency spectral components whose central frequencies are different from each other are generated. Using a difference between the spectral components makes it possible to derive sequential values of spectral phases of pulsed object light E6, and to calculate a refractive index of the measured object 200C by the spectral phases.

The detector 140C calculates a refractive index of the measured object 200B, based on a sum frequency C8. More specifically, the detector 140C calculates a refractive index of the measured object 200C, based on interference in a spectral domain, which is generated by generation of a sum frequency C8. The detector 140C included by a spectral measurement device, for instance. The spectral measurement device detects a light intensity in a spectral domain of the sum frequency C8.

When time resolution of a spectral measurement device is sufficiently large as compared with a time when the phase of reference light E(R) is adjusted, the spectral measurement device can simultaneously detect two sum frequency spectral components, and measure interference fringes in a spectral domain where the two spectral components interfere with each other.

Note that in deriving a spectral phase, interference fringes in a spectral domain of a second harmonic, which is generated when a distributed pulse PD is not allowed to be incident on the non-linear optical crystal 150 and only interference light E2 is incident, are acquired in advance. It is possible to extract a spectral phase by subtracting the amount of phase adjusted in reference light E(R), which can be derived from an interference image of the second harmonic, from information on interference fringes in a spectral domain by two sum frequency spectral components.

Next, an operation of the light measurement device 100C is described.

As well as the content described using FIG. 2, positions of the first lens 110, the phase adjustment unit 120C, the second lens 130, the non-linear optical crystal 150, and the detector 140C are adjusted. In this way, controlling optical axis adjustment and the amount of light for splitting independently of each other makes it easy to attain light amount uniformity of two beams (signal light and reference light). Therefore, it is possible to increase brightness of interference fringes by the sum frequencies C8 to be detected by the detector 140C. Further, it is easy to eliminate a deviation difference regarding an image forming position (an image forming position by the sum frequencies C8 in the detector 140C) in accordance with a phase shift amount.

First of all, pulsed light PC is incident on the measured object 200C as light source light. When pulsed light PC transmits or reflects with respect to the measured object 200C, pulsed object light E6 is generated. Specifically, pulsed object light E6 is light to be obtained by transmission or reflection of pulsed light PC with respect to the measured object 200C.

Further, pulsed object light E6 is incident on the first lens 110. The first lens 110 converts incident pulsed object light E6 into a parallel light flux. Pulsed object light E6, which is converted into a parallel light flux by the first lens 110, is incident on the phase adjustment unit 120C.

For instance, the phase adjustment unit 120C adjusts the phase of pulsed object light E6 to be incident on an upper portion (on the upper side on the plane of FIG. 6) of the phase adjustment unit 120C. On the other hand, the phase adjustment unit 120C does not adjust the phase of the pulsed object light E6 to be incident on a lower portion (on the lower side on the plane of FIG. 6) of the phase adjustment unit 120C.

Next, the phase adjustment unit 120C outputs reference light E(R) after phase adjustment from an upper area of the phase adjustment unit 120C, and outputs signal light E(S) whose phase is not adjusted from a lower area of the phase adjustment unit 120C.

Note that, for instance, in a case where the sectional area of the phase adjustment unit 120C in an optical axis direction is small, as compared with the beam diameter of pulsed object light E6 from the measured object 200C, it is possible to omit the first lens 110. Specifically, in a case where pulsed object light E6 to be incident on the phase adjustment unit 120C is regarded as a parallel light flux, it is possible to allow incidence of the pulsed object light E6 into the phase adjustment unit 120C without converting the pulsed object light E6 into a parallel light flux. In a case where the measured object 200C is disposed far from the phase adjustment unit 120C, it is also possible to omit the first lens 110 for the same reason as described above. Signal light E(S) and reference light E(R) output by the phase adjustment unit 120C are incident on the second lens 130.

Next, the second lens 130 collects signal light E(S) and reference light E(R) to be output from the phase adjustment unit 120B on the non-linear optical crystal 150. Specifically, the second lens 130 collects, on the non-linear optical crystal 150, interference light E2 between reference light E(R) after phase adjustment by the phase adjustment unit 120C, and signal light E(S) whose phase is not adjusted by the phase adjustment unit 120C. Further, a distributed pulse PD is incident on the non-linear optical crystal 150. Then, interference light E2 generated by collecting light on the second lens 130, and the distributed pulse PD are incident on the non-linear optical crystal 150. Specifically, signal light E(S) to be output by the phase adjustment unit 120C, reference light E(R) to be output by the phase adjustment unit 120C, and a distributed pulse BP are incident into the non-linear optical crystal 150. Then, two sum frequencies C8 between reference light E(R), signal light E(S), and the distributed pulse BP are generated.

The sum frequencies C8 is incident on the detector 140C. The detector 140C derives a refractive index of the measured object 200C, based on the sum frequencies C8. More specifically, the detector 140C derives a refractive index of the measured object 200C, based on interference in a spectral domain, which is generated by generation of the sum frequencies C8. In this case, the detector 140C detects interference in a spectral domain, which is generated by the sum frequencies C8, and derives a refractive index of the measured object 200C from the interference in the spectral domain. Note that a specific derivation method is the same as in the second example embodiment.

Herein, a central frequency of the distributed pulse PD changes with time. Therefore, in deriving a refractive index of the measured object 200C, on the non-linear optical crystal 150, the frequency of the sum frequencies C8 to be generated between the distributed pulse PD and reference light, and the frequency of the sum frequencies C8 to be generated between the distributed pulse PD and signal light are different from each other.

The detector 140C measures interference fringes in a spectral domain of two sum frequencies whose frequencies are different from each other as described above. Thus, the detector 140 derives sequential values of spectral phases.

The foregoing is description about an operation of the light measurement device 100C.

As described above, the light measurement device 100C in the third exemplary embodiment of the present invention further includes the non-linear optical crystal 150. The non-linear optical crystal 150 is disposed between the phase adjustment unit 120C and the detector 140C. Light from a light source is pulsed light PL including excitation light. The phase adjustment unit 120C adjusts the phase between signal light E(S) and reference light E(R) by using pulsed object light E6 being light to be obtained by transmission or reflection of pulsed light PL with respect to the measured object 200C as the signal light E(S), and by using light E6 whose phase is adjusted with respect to the pulsed object light E6 as the reference light E(R). Reference light E6(R) and signal light E(S) are incident on the non-linear optical component 150, and a distributed pulse PD is incident on the non-linear optical component 150. The detector 140C is a spectral measurement device configured to derive a refractive index of the measured object 200C, based on two sum frequencies C8 generated between signal light E(S), reference light E(R), and the distributed pulse PD after transmission through the non-linear optical component 150.

In this way, in the light measurement device 100C, the phase adjustment unit 120C outputs both of reference light E(R) after phase adjustment, and signal light E(S) whose phase is not adjusted. Therefore, as well as the aforementioned content, it is possible to measure a refractive index of the measured object 200C with a simplified configuration.

In this case, in the light measurement device 100C, reference light E(R) after phase adjustment, signal light E(S) whose phase is not adjusted, and the distributed pulse PD are incident on the non-linear optical crystal 150. Therefore, it is possible to generate two sum frequencies C8 between reference light E(R), signal light E(S), and the distributed pulse PD within the non-linear optical crystal 150. Thus, it is possible to derive, by the detector 140C, a refractive index of the measured object 200C, based on interference fringes in a spectral domain by the generated two sum frequencies C8. In this case, the detector 140C can detect interference fringes in a spectral domain generated by the sum frequencies C8, and derive a refractive index of the measured object 200C from interference in the spectral domain.

Fourth Exemplary Embodiment

FIG. 7 is a diagram schematically illustrating a configuration of a light measurement device 100D in the fourth exemplary embodiment of the present invention. Note that in FIG. 7, constituent elements equivalent to the constituent elements illustrated in FIG. 1 to FIG. 6 are indicated by the same reference numerals as the reference numerals illustrated in FIG. 1 to FIG. 6.

As illustrated in FIG. 7, the light measurement device 100D includes a first lens 110, a polarization beam splitter 160, a phase adjustment unit 120C, a second lens 130, a first detector 141, a third lens 170, and a second detector 142. Note that the first lens 110, the second lens 130, and the third lens 170 may be omitted as well as the content described using FIG. 1.

As illustrated in FIG. 7, a measured object 200 is disposed on the front side of the first lens 110, as a measurement object for the light measurement device 100D. Examples of the measured object 200 are a liquid and a living body. The measured object 200, however, is not limited to the above, as far as the measured object transmits or reflects light. When light E from a light source transmits or reflects with respect to the measured object 200, object light E1 is generated. Specifically, object light E1 is light to be obtained when light E from a light source transmits or reflects with respect to the measured object 200.

Herein, comparison is made between FIG. 1 and FIG. 7. FIG. 7 is different from FIG. 1 in a point that the polarization beam splitter 160 is disposed between the first lens 110 and the phase adjustment unit 120. Further, in FIG. 1, only one detector 140 is provided. On the other hand, in FIG. 7, two detectors 141 and 142 are provided. In this point, FIG. 1 and FIG. 7 are different from each other. Further, FIG. 7 is different from FIG. 1 in a point that the third lens 170 is provided.

As illustrated in FIG. 7, the first lens 110, the polarization beam splitter 160, the phase adjustment unit 120, the second lens 130, and the first detector 141 are disposed along the optical axis of light source light E. The optical axis of light source light E is linearly disposed. Further, the third lens 170 and the second detector 142 are disposed along the optical axis of light E1 split by the polarization beam splitter 160. The optical axis of light E1 split by the polarization beam splitter 160 is linearly disposed.

As illustrated in FIG. 7, the first lens 110 is disposed between the measured object 200 and the polarization beam splitter 160. Further, the first lens 110 is disposed on the optical axis of object light E1. Light source light E is incident on the first lens 110. Further, the first lens 110 converts incident object light E1 into a parallel light flux, and outputs the parallel light flux to the polarization beam splitter 160.

As illustrated in FIG. 7, the polarization beam splitter 160 is disposed between the first lens 110 and the phase adjustment unit 120. The polarization beam splitter 160 splits object light E1 to be output by the first lens 110 in two directions. One beam of object light E1 split by the polarization beam splitter 160 is output by the polarization beam splitter 160 in a direction of the phase adjustment unit 120, the second lens 130, and the first detector 141. The other beam of object light E1 split by the polarization beam splitter 160 is output by the polarization beam splitter 160 in a direction of the third lens 170 and the second detector 142.

As illustrated in FIG. 7, the phase adjustment unit 120 is disposed between the polarization beam splitter 160 and the second lens 130. Further, the phase adjustment unit 120 is disposed on the optical axis of object light E1. Object light E1 to be output by the polarization beam splitter 160 is incident in both of an upper area (on the upper side on the plane of FIG. 7) and a lower area (on the lower side on the plane of FIG. 7) of the phase adjustment unit 120. The phase adjustment unit 120 adjusts the phase of a part of incident light. The phase adjustment unit 120 adjusts the phase difference between signal light E(S) based on object light E1 being light to be obtained by transmission or reflection of light from a light source with respect to the measured object 200, and reference light E(R) for use in obtaining interference light E2 with respect to the signal light E(S).

Herein, as well as the content described using FIG. 1, the phase adjustment unit 120 generates a phase difference between an upper portion of object light E1 and a lower portion of the object light E1 by applying different modulations to the upper portion (on the upper side on the plane of FIG. 7) of the object light E1 with respect to the center of the phase adjustment unit 120, and to the lower portion (on the lower side on the plane of FIG. 7) of the object light E1 with respect to the center of the phase adjustment unit 120. For instance, the phase adjustment unit 120 may generate a phase difference by modulating both of an upper portion (on the upper side on the plane of FIG. 7) of object light E1 with respect to the center of the phase adjustment unit 120, and a lower portion (on the lower side on the plane of FIG. 7) of the object light E1 with respect to the center of the phase adjustment unit 120. Alternatively, the phase adjustment unit 120 may adjust the phase of an upper portion (on the upper side on the plane of FIG. 7) of object light E1 with respect to the center of the phase adjustment unit 120 by modulating only the upper portion (on the upper side on the plane of FIG. 7) of the object light E1 with respect to the center of the phase adjustment unit 120, and may not adjust the phase of a lower portion (on the lower side on the plane of FIG. 7) of the object light E1 with respect to the center of the phase adjustment unit 120.

Note that the exemplary embodiment is not limited to the above. The phase adjustment unit 120 may adjust the phase of a lower portion (on the lower side on the plane of FIG. 7) of object light E1 with respect to the center of the optical path of the object light E1, and may not adjust the phase of an upper portion (on the upper side on the plane of FIG. 7) of the object light E1 with respect to the center of light of the object light E1. In a case where the phase adjustment unit 120 modulates only an upper portion (on the upper side on the plane of FIG. 7) or a lower portion (on the lower side on the plane of FIG. 7) of object light E1 with respect to the center of the phase adjustment unit 120, for instance, the phase adjustment unit 120 outputs object light E1 after phase adjustment by the phase adjustment unit 120 as reference light E(R), and outputs object light E1 whose phase is not adjusted by the phase adjustment unit 120 as signal light E(S).

In this case, the phase adjustment unit 120 adjusts and outputs light in such a manner that the light amount of reference light E(R) after phase adjustment to be output from an upper area (on the upper side on the plane of FIG. 7) of the phase adjustment unit 120 with respect to the center of the phase adjustment unit 120 is equal to the light amount of signal light E(S) to be output from a lower area (on the lower side on the plane of FIG. 7) of the phase adjustment unit 120 with respect to the center of the phase adjustment unit 120. Note that as described using FIG. 1, the phase adjustment unit 120 includes a spatial light modulator. Detailed description on a configuration or the like of the spatial light modulator is the same as described using FIG. 1, and therefore, is omitted.

As illustrated in FIG. 7, the second lens 130 is disposed between the phase adjustment unit 120 and the first detector 141. The second lens 130 collects reference light E(R) and signal light E(S) to be output from the phase adjustment unit 120. Specifically, the second lens 130 collects reference light E(R) after phase adjustment by the phase adjustment unit 120, and signal light E(S) whose phase is not adjusted.

According to the aforementioned configuration, it is possible to detect, by the detector 141, light (interference light E2) generated by interference between reference light E(R) and signal light E(S) to be output by the phase adjustment unit 120. Specifically, interference light E2 is generated by interference between reference light E(R) after phase adjustment by the phase adjustment unit 120, and signal light E(S) whose phase is not adjusted. The interference light E2 is incident on the first detector 141.

As illustrated in FIG. 7, the first detector 141 is disposed to face the second lens 130. Interference light E2 collected by the second lens 130 is incident on the first detector 141. The first detector 141 detects interference light E2 between reference light E(R) and signal light E(S), and derives a light intensity distribution or a refractive index of the measured object 200, based on the detected interference light E2.

As illustrated in FIG. 7, the third lens 170 is disposed along a direction orthogonal to the optical path of light E from a light source. The third lens 170 is disposed to face the polarization beam splitter 160. The third lens 170 collects object light E1 split by the polarization beam splitter 160 toward the second detector 142.

As illustrated in FIG. 7, the second detector 142 is disposed to face the third lens 170. The second detector 142 derives a light intensity distribution or a refractive index of the measured object 200, based on light collected by the third lens 170.

Next, an operation of the light measurement device 100D is described.

First of all, light E from a light source is incident on the measured object 200. When light source light E transmits or reflects with respect to the measured object 200, object light E1 is generated.

Further, object light E1 is incident on the first lens 110. The first lens 110 converts incident object light E1 into a parallel light flux. Object light E1, which is converted into a parallel light flux by the first lens 110, is incident on the polarization beam splitter 160.

The polarization beam splitter 160 splits object light E1 in two directions. One beam of object light E1 split by the polarization beam splitter 160 is output by the polarization beam splitter 160 in a direction of the phase adjustment unit 120, the second lens 130, and the first detector 141. The other beam of object light E1 split by the polarization beam splitter 160 is output by the polarization beam splitter 160 in a direction of the third lens 170 and the second detector 142.

One beam of object light E1 split by the polarization beam splitter 160 is incident on the phase adjustment unit 120. The phase adjustment unit 120 adjusts the phase of a part of object light E1. Specifically, for instance, the phase adjustment unit 120 adjusts the phase of object light E1 in an upper area (on the upper side on the plane of FIG. 7) of the phase adjustment unit 120, and does not adjust the phase of object light E1 in a lower area (on the lower side on the plane of FIG. 7) of the phase adjustment unit 120.

The phase adjustment unit 120 outputs reference light E(R) after phase adjustment from an upper area of the phase adjustment unit 120, and outputs signal light E(S) whose phase is not adjusted from a lower area of the phase adjustment unit 120. Signal light E(S) and reference light E(R) output by the phase adjustment unit 120 are incident on the second lens 130.

The second lens 130 collects signal light E(S) and reference light E(R) to be output from the phase adjustment unit 120 on the first detector 141. Specifically, the second lens 130 collects reference light E(R) after phase adjustment by the phase adjustment unit 120, and signal light E(S) whose phase is not adjusted. Then, signal light E(S) and reference light E(R) to be output from the phase adjustment unit 120 interfere with each other. Specifically, reference light E(R) and signal light E(S) interfere with each other, and interference light E2 is generated. Interference light E2 is incident on the first detector 141.

The detector 141 detects interference light E2 between reference light E(R) and signal light E(S), and derives a light intensity distribution or a refractive index of the measured object 200, based on the detected interference light E2.

The other beam of object light E1 split by the polarization beam splitter 160 is incident on the third lens 170.

The third lens 170 collects the other beam of object light E1 split by the polarization beam splitter 160 on the second detector 142. Further, the detector 142 derives a light intensity distribution or a refractive index of the measured object 200, based on incident light.

The foregoing is description about an operation of the light measurement device 100D.

Note that disposing a measured object at a midway of an optical path as illustrated in FIG. 3, for instance, by using the configuration illustrated in FIG. 7 as a basic configuration, makes it possible to acquire a light intensity distribution of the measured object in an optical axis direction. Further, combining the configuration illustrated in FIG. 4 by using the configuration illustrated in FIG. 7 as a basic configuration makes it possible to measure a reflection light intensity distribution of a measured object in an optical axis direction. Further, combining the configuration illustrated in FIG. 5 by using the configuration illustrated in FIG. 7 as a basic configuration makes it possible to derive a change in the refractive index, which is generated in a measured object from a difference in spectral interference fringes due to the presence or absence of incidence of excitation light. Further, combining the configuration illustrated in FIG. 6 by using the configuration illustrated in FIG. 7 as a basic configuration makes it possible to measure a refractive index of a measured object.

As described above, the light measurement device 100D in the fourth exemplary embodiment of the present invention includes the polarization beam splitter 160. The polarization beam splitter 160 is disposed along light E from a light source at a position between the measured object 200 and the first detector 141. The polarization beam splitter 160 splits object light E1. Thus, it is possible to measure a refractive index of the measured object 200 by using a plurality of light beams split by the polarization beam splitter 160.

Further, the light measurement device 100D in the fourth exemplary embodiment of the present invention may further include a plurality of phase adjustment units 120. In this case, the plurality of phase adjustment units 120 are disposed along optical axes of a plurality of beams of object light E1 split by the polarization beam splitter 160. The plurality of phase adjustment units 120 adjust respective phases of the plurality of beams of object light E1. Thus, it is possible to generate a plurality of beams of interference light E2 whose phases are different from each other.

Fifth Exemplary Embodiment

A configuration of a Mach-Zehnder modulator in the fifth exemplary embodiment of the present invention is described. The basic configuration of the modulator is the same as the configuration of the light measurement device 100 illustrated in FIG. 1. However, continuous light whose intensity is constant propagates in a direction of a first lens 110 like object light E1 in FIG. 1, while keeping light source light E unchanged without disposing a measured object 200. The following description is made based on the premise that object light E1 in FIG. 1 is continuous light.

Specifically, as described in the configuration illustrated in FIG. 1, it is also possible to cause the Mach-Zehnder modulator to function as a modulator by providing a first lens 110, a phase adjustment unit 120, a second lens 130, and a detector 140.

First of all, it is assumed that the measured object 200 is not disposed in FIG. 1. In this case, light source light E is unchanged, and continuous light E1 whose intensity is constant propagates in a direction of the first lens 110 like object light E1 in FIG. 1, and is incident on the first lens 110.

The first lens 110 converts continuous light E1 whose intensity is constant into a parallel light flux. Further, continuous light E1, which is converted into a parallel light flux by the first lens 110, is incident on the phase adjustment unit 120.

The phase adjustment unit 120 adjusts, for example, the phase of an upper portion (on the upper side on the plane of FIG. 1) of continuous light E1 with respect to the center of the phase adjustment unit 120. On the other hand, the phase adjustment unit 120 does not adjust the phase of a lower portion (on the lower side on the plane of FIG. 1) of the continuous light E1 with respect to the center of the phase adjustment unit 120.

The phase adjustment unit 120 outputs signal light E(S) after phase adjustment by the phase adjustment unit 120, and reference light E(R) whose phase is not adjusted toward the second lens 130.

Herein, in the aforementioned section "Exemplary Embodiment Illustrating Concept", light after phase adjustment by the phase adjustment unit 120 is referred to as reference light E(R), and light whose phase is not adjusted is referred to as signal light E(S). On the other hand, in the exemplary embodiment, light after phase adjustment by the phase adjustment unit 120 is referred to as signal light E(S), and light whose phase is not adjusted is referred to as reference light E(R).

Next, the second lens 130 collects reference light E(R) and signal light E(S) to be output from the phase adjustment unit 120. Then, reference light E(R) and signal light E(S) to be output by the phase adjustment unit 120 interfere with each other. Specifically, reference light E(R) and signal light E(S) interfere with each other, and interference light E2 is generated as modulated light. Specifically, by allowing continuous light E1 to pass through the first lens 110, the phase adjustment unit 120, and the second lens 130, the continuous light E1 turns to modulated light (interference light E2) having an intensity variation. The modulated light (interference light E2) is incident on the detector 140.

The detector 140 as a receiving unit receives modulated light (interference light E2) between reference light E(R) and signal light E(S). Further, the detector 140 detects the modulated light (interference light E2), and receives a modulated signal in accordance with modulation of an electrical signal imparted by the phase adjustment unit 120, based on the detected modulated light (interference light E2). Note that the first lens 110 and the second lens 130 may be omitted as well as the content described using FIG. 1.

Generally, there is an electro-optical modulator using carrier plasma effects, as a Mach-Zehnder modulator using light interference. An electro-optical modulator imparts a timewise change to a refractive index by input of an electrical signal such as a voltage with respect to an optical waveguide or the like having an electrical structure such that a carrier density changes, with use of carrier plasma effects. As a result of changing the refractive index of an optical waveguide, a phase change occurs with respect to light propagating through the optical waveguide. This phase change is converted into an intensity variation by being incorporated in a Mach Zehnder interferometer or the like. The intensity of input continuous light is modulated by a Mach Zehnder interferometer, and the modulated continuous light is output as modulated light.

A Mach Zehnder modulator as described above includes two arms constituting a Mach Zehnder interferometer. Each of the two arms serves as an optical path having no branch or the like. After splitting and propagation through the two arms, continuous light input to the Mach Zehnder modulator is combined again by a light coupler or the like for output. Further, each of the two arms has a structure such that the refractive index is changed within each of the optical paths. For instance, an electrode for changing the refractive index is provided substantially in the whole area of the arm within an optical waveguide. Further, an electric field is applied to each arm via each electrode to change the refractive index of the optical waveguide, whereby the phase of light propagating through each arm is changed, a phase difference is generated with respect to light propagating through each arm, and the intensity of light to be output is changed by causing interference between these light components.

For instance, object light E1 in FIG. 1 is used as continuous light whose intensity is constant, and the phase adjustment unit 120 adjusts the phase of continuous light after passing through the first lens 110 in an upper area (on the upper side on the plane of FIG. 1) of the phase adjustment unit 120, and does not adjust the phase of the continuous light in a lower area (on the lower side on the plane of FIG. 1) of the phase adjustment unit 120. In this case, the phase is timewise adjusted by timewise changing the refractive index by input of an electrical signal such as a voltage from the outside. Light whose phase is adjusted and light whose phase is not adjusted are collected on the detector 140, which is disposed as a receiving unit, through the second lens 130. Interference light to be detected by the detector 140 serves as a modulated signal in accordance with modulation of an electrical signal imparted by the phase adjustment unit 120, as well as a Mach Zehnder modulator.

In addition to the above, the phase may be adjusted by the phase adjustment unit 120, and information may be acquired by Fourier transforming a signal obtained by the detector 140.

As above, the present invention has been described based on the exemplary embodiments. An exemplary embodiment is just an illustration, and various kinds of changes, addition or subtraction and combinations may be added to each of the above-mentioned exemplary embodiments unless it deviates from the main points of the present invention. It is understood by a person skilled in the art that modification made by adding such changes, addition/subtraction and combinations are also included in the scope of the present invention.

In the foregoing, the invention of the present application is described with reference to the exemplary embodiments (and examples). The invention of the present application, however, is not limited to the foregoing exemplary embodiments (and examples). The configuration and the details of the invention of the present application may be modified in various ways comprehensible to a person skilled in the art within the scope of the invention of the present application.

This application claims the priority based on Japanese Patent Application No. 2015-062054 filed on Mar. 25, 2015, entire disclosure of which is hereby incorporated.

REFERENCE SIGNS LIST 100, 100A, 100AA, 100B, 100C, 100D Light measurement device
110 First lens
120, 120A, 120B, 120C Phase adjustment unit
130 Second lens
140, 140A, 140B, 140C Detector
141 First detector
142 Second detector
150 Non-linear optical crystal
160 Polarization beam splitter
170 Third lens
180 Outer mirror
190a, 190b, 190c, 190d Inner mirror
200, 200A, 200B, 200C Measured object
300 Light source
E Light from light source, light source light
E1 Object light
E2 Interference light
E(R) Reference light
E(S) Signal light
ER Excitation ray
E4 Excitation object light
PL Pulsed light
E6 Pulsed object light
PD Distributed pulse
C8 Sum frequency

The invention claimed is:

1. A light measurement device comprising:
a light modulator configured to adjust a phase difference between signal light, which is based on object light being light to be obtained by causing light from a light source to transmit through or be reflected from a measured object, and reference light which is light for use in obtaining interference light with the signal light, by applying different modulations between the signal light and the reference light; and
a detector configured to detect interference light between the signal light and the reference light output from the phase adjustment unit, and derive a reflection light intensity distribution or a refractive index of the measured object, based on the interference light, wherein
an optical axis of the light from the light source or the object light is linearly disposed, and
the light modulator and the detector are disposed on the optical axis of the light from the light source or the object light.

2. The light measurement device according to claim 1, wherein
the light modulator adjusts a phase difference between the signal light and the reference light by using light that is the object light whose phase is adjusted, as the reference light, and by using light that is the object light whose phase is not adjusted, as the signal light.

3. The light measurement device according to claim 1, wherein
the light modulator adjusts a phase difference between the signal light and the reference light by using light that is the object light whose phase is adjusted, as the reference light, and by using light that is the object light whose phase is not adjusted, as the reference light, and
the detector derives a reflection or transmission light intensity distribution with respect to the measured object, based on interference light between the signal light and the reference light.

4. The light measurement device according to claim 1, wherein
excitation light is incident on the measured object,
the light modulator adjusts a phase difference between the signal light and the reference light by using excitation object light being light obtained by transmission or reflection of the light from the light source and the excitation light with respect to the measured object, as the signal light, and by using light that is the light from the light source whose phase is adjusted, as the reference light, and
the detector is a spectral measurement device configured to derive a change in a refractive index of the measured object, based on interference light between the signal light and the reference light.

5. The light measurement device according to claim 1, further comprising:
a non-linear optical crystal disposed between the light modulator and the detector, wherein
the light from the light source is pulsed light,
the light modulator adjusts a phase difference between the signal light and the reference light by using pulsed object light being light obtained by transmission or reflection of the pulsed light with respect to the measured object, as the signal light, and by using light that is the pulsed light whose phase is adjusted, as the reference light, the signal light and the reference light are incident on the non-linear optical component, and a distributed pulse is incident on the non-linear optical component, and the detector is a spectral measurement device configured to derive a refractive index of the measured object, based on sum frequencies generated between the signal light, the reference light, and the distributed pulse after transmission through the non-linear optical component.

6. The light measurement device according to claim 1, further comprising:

a polarization beam splitter disposed along an optical path between the measured object and the detector to split the object light.

7. The light measurement device according to claim 6, further comprising:

a plurality of the light modulator, wherein the plurality of light modulator is disposed on optical axes of a plurality of beams of object light split by the polarization beam splitter and adjusts a phase of each of the plurality of beams of object light.

8. The light measurement device according to claim 1, wherein a plurality of the light modulator is disposed in series along the optical axis of the light from the light source between the measured object and the detector.

9. The light measurement device according to claim 1, wherein the light modulator includes a spatial light modulator, and the spatial light modulator includes a liquid crystal unit, and changes an optical path length of a part of incident light by partially changing a refractive index of the liquid crystal unit.

10. The light measurement device according to claim 9, wherein the liquid crystal unit is formed by a micro-optical element.

11. The light measurement device according to claim 1, wherein the light source and the detector operate in a visible range.

12. An electro-optical modulator comprising:

the light measurement device according to claim 1, wherein the electro-optical modulator applies modulation to the light modulator by an electrical signal, and interference light between the signal light and the reference light output from the phase light modulator, is used as a modulated signal.

13. An electro-optical modulator comprising:

a light measurement device comprising:

a light modulator configured to adjust a phase difference between signal light and reference light, the signal light being based on object light being light to be obtained by causing light from a light source to transmit through or be reflected from a measured object, the reference light being light for use in obtaining interference light with the signal light; and a detector configured to detect interference light between the signal light and the reference light output from the phase adjustment unit, and derive a reflection light intensity distribution or a refractive index of the measured object, based on the interference light, wherein an optical axis of the light from the light source or the object light is linearly disposed, the light modulator and the detector are disposed on the optical axis of the light from the light source or the object light, the electro-optical modulator applies modulation to the light modulator by an electrical signal, and interference light between the signal light and the reference light output from the phase adjustment unit, is used as a modulated signal.

* * * * *